US007853058B2

(12) United States Patent
Gauldie et al.

(10) Patent No.: US 7,853,058 B2
(45) Date of Patent: Dec. 14, 2010

(54) DETERMINING A VIEWPOINT FOR NAVIGATING A VIRTUAL CAMERA THROUGH A BIOLOGICAL OBJECT WITH A LUMEN

(75) Inventors: David Gauldie, Edinburgh (GB); David Mayne, Edinburgh (GB); Swati Mital, Edinburgh (GB); Thomas MacArthur Winter Doel, Edinburgh (GB); Kristopher Thomas Cruickshank, Edinburgh (GB)

(73) Assignee: Toshiba Medical Visualization Systems Europe, Limited, Edinburgh (GB)

( * ) Notice: Subject to any disclaimer, the term of this patent is extended or adjusted under 35 U.S.C. 154(b) by 1057 days.

(21) Appl. No.: 11/562,570

(22) Filed: Nov. 22, 2006

(65) Prior Publication Data

US 2008/0118117 A1 May 22, 2008

(51) Int. Cl.
*G06K 9/00* (2006.01)
(52) U.S. Cl. .................. 382/128; 382/100; 382/131; 382/154; 345/419; 345/424; 345/427; 434/262; 434/267; 600/101; 600/114; 600/300; 600/407
(58) Field of Classification Search .................. None
See application file for complete search history.

(56) References Cited

U.S. PATENT DOCUMENTS

| 5,611,025 A | 3/1997 | Lorensen et al. |
| 5,782,762 A | 7/1998 | Vining |
| 5,971,767 A | 10/1999 | Kaufman et al. |
| 6,083,162 A | 7/2000 | Vining |

(Continued)

FOREIGN PATENT DOCUMENTS

| WO | WO 98/32371 | 7/1998 |
| WO | WO 03/046811 | 6/2003 |
| WO | WO 03054803 | 7/2003 |

OTHER PUBLICATIONS

Wyatt, C.L. et al., "Automatic Segmentation of the Colon for Virtual Colonoscopy", Computerized Medical Imaging and Graphics, 1, 1-9, 2000.

(Continued)

*Primary Examiner*—Andrew W Johns
*Assistant Examiner*—Jason Heidemann
(74) *Attorney, Agent, or Firm*—Renner, Otto, Boisselle & Sklar LLP

(57) ABSTRACT

A method of orienting a virtual camera for rendering a virtual endoscopy image of a lumen in a biological structure represented by a medical image data set, e.g., a colon. The method comprises selecting a location from which to render an image, determining an initial orientation for the virtual camera relative to the data set for the selected location based on the geometry of the lumen, determining an offset angle between the initial orientation and a bias direction; and orienting the virtual camera in accordance with a rotation from the initial orientation towards the bias direction by a fractional amount of the offset angle which varies according to the initial orientation. The fractional amount may vary according to the offset angle and/or a separation between a predetermined direction in the data set and a view direction of the virtual camera for the initial orientation. Thus the camera orientation can be configured to tend towards a preferred direction in the data set, while maintaining a good view of the lumen and avoiding barrel rolling effects.

39 Claims, 9 Drawing Sheets

U.S. PATENT DOCUMENTS

| | | | |
|---|---|---|---|
| 6,343,936 | B1 | 2/2002 | Kaufman et al. |
| 6,346,940 | B1 | 2/2002 | Fukunaga |
| 6,496,188 | B1 | 12/2002 | Deschamps et al. |
| 2003/0152897 | A1* | 8/2003 | Geiger .................. 434/262 |
| 2004/0202990 | A1 | 10/2004 | Geiger |
| 2004/0209234 | A1* | 10/2004 | Geiger .................. 434/262 |
| 2005/0033114 | A1 | 2/2005 | Geiger et al. |
| 2005/0148848 | A1* | 7/2005 | Guang et al. .......... 600/407 |
| 2005/0187432 | A1 | 8/2005 | Hale et al. |
| 2005/0251017 | A1 | 11/2005 | Azar |
| 2007/0052724 | A1* | 3/2007 | Graham et al. ........ 345/620 |

OTHER PUBLICATIONS

Frimmel, H. et al., "Centerline-Based Colon Segmentation for CT Colongraphy", Medical Physics, 32, 8, 2665-2672.

Bartz, D., "Virtual Endoscopy in Research and Clinical Practice", STAR—State of the Art Report, Eurographics 2003, The Eurographics Association, 27 pages.

Huang, A. et al., Teniae Coli Guided Navigation and Registration for Virtual Colonoscopy IEEE, Visualization 2005: 36, 7 pages.

Summers, Ronald M., "Navigational Aids for Real-Time Virtual Bronchoscopy," Computers in Radiology, AJR:168, May 1997, 1165-1170.

* cited by examiner

DETERMINING A VIEWPOINT FOR NAVIGATING A VIRTUAL CAMERA THROUGH A BIOLOGICAL OBJECT WITH A LUMEN

BACKGROUND ART

The invention relates to the virtual endoscopy, and in particular to determining a viewpoint for navigating a virtual camera through a biological object with a lumen.

Traditional endoscopy involves the use of an endoscope which is inserted into a patient to allow direct visual inspection of, for example, the colon. The technique is relatively invasive and uncomfortable, and often requires heavy patient sedation. Accordingly, virtual endoscopy, which is based on an analysis of medical image data (computer simulated endoscopy), is often preferred.

Patient medical imaging methods, such as computer-assisted tomography (CT), magnetic resonance imaging (MRI), ultrasound and positron-emission tomography (PET), generate large three-dimensional (3D) volume data sets representing all or part of a patient's body. These volume data sets are highly detailed and allow complex studies of the body to be made. Virtual endoscopy is a technique in which a virtual camera is made to travel along a biological object with a lumen (such as a colon, blood vessel or bronchial tree), with the image of the lumen seen by the virtual camera presented to a user for diagnostic and other purposes. Virtual endoscopy is less invasive for the patient and provides the clinician with a much greater degree of flexibility in the way he can view the lumen of interest. For example, the clinician can choose to observe the virtual lumen from almost any direction and on any scale.

A common analysis technique for medical image data is therefore to render a series of two-dimensional images from the viewpoint of a camera travelling along a path within a lumen of interest. The series of images may be displayed to a clinician in sequence to provide a virtual "fly-through" of the lumen of interest. To navigate the viewpoint through the lumen, a path for the virtual camera to follow is usually determined in advance because even experienced clinicians can have difficulty in manually controlling the virtual camera movement in real time.

There are a number of well-known methods for calculating suitable paths for the camera to follow. These paths are frequently referred to as centerlines because they are usually designed to follow as closely as possible a central route through the lumen. Methods for calculating suitable paths include those based on mathematical techniques designed for wall avoidance [1, 2], those based on mathematical techniques that use erosion to determine a centerline along a lumen [3], those based on labeling points in the data set with their distance from an end of the path using a wavefront model to avoid obstacles and calculating the path by moving from point to point according to the closest distance to the end point [4], those based on obtaining an initial path by using a distance label map to connect start and end voxels in the data set via intermediate voxels according to their distance from the start and end voxels, and then centering the path using maximum diameter spheres [5, 6], and those based on determining navigation steps by using ray casting to find the longest ray from a camera position to the wall and weighting this with the existing viewing direction of the camera to obtain a new direction for movement of the camera, and repeating this for each step [7]. General data collection and processing methods for viewing three-dimensional patient images have also been described [8, 9]. A number of commercial virtual endoscopy systems and the various approaches taken to camera navigation and to the image processing necessary to represent a realistic view of the lumen are discussed by Bartz [10].

Once the locus of the flight path (centerline) is determined, a number of locations along the path are selected as locations from which to render images that will comprise frames in the virtual flythrough of the lumen. Thus the flythrough comprises images rendered from locations corresponding to incremental steps along the flight path. For a colon, the locations for generating images will typically be evenly spaced along the flight path with separations (i.e. step sizes) on the order of 1 mm or so.

In addition to selecting locations for the virtual camera position, it is also necessary to select a view direction (i.e. orientation) for the camera to render the images. Conventionally the camera will be oriented so that it points towards a location on the flight path a fixed distance ahead of its current position. Thus, at the start location the virtual camera will be oriented so that its view vector is directed towards a position on the flight path that the camera will reach in, say, four steps time. The orientation of the camera about its view vector (roll angle) at the initial location will typically be selected arbitrarily. Once an image has been rendered for the initial location and camera orientation, the virtual camera undergoes a translation movement to take it to the next location on the flight path. After the translation, the camera orientation will be such that it will not be pointing along the desired view direction for the new location (at least in the general case). Accordingly, the camera is re-oriented so that it again points towards a position which is the selected fixed distance ahead of the camera's present location on the flight path (e.g. four steps ahead in this example). This can be achieved using conventional vector algebra, and, depending on the shape of the flight path, the camera rotation may include components about any of the camera's pitch, roll or yaw axes. An image may then be rendered which corresponds to the camera's new location and view direction. The camera then moves to the next location along the flight path, where the process is repeated. This continues until the camera completes the fly through (i.e. reaches the last location on the flight path).

A problem with this approach is that the flythrough view can become disorientating for a viewer as the virtual camera rolls, pitches and yaws along what is typically a complex path of loops, twists and turns. This can hinder the interpretation of the data and in some cases can even cause nausea for the clinician viewing the data.

A further problem arises when a clinician wishes to compare different data sets representing the same lumen. There are a number of reasons why a clinician may want to do this. For example, medical image data will typically be obtained with the patient in a range of orientations, e.g., on his back (supine), on his front (prone), and/or on his side(s) (lateral decubitus). A clinician will usually want to compare flythroughs of all available data sets for these orientations to allow a thorough examination of the lumen. In other cases there may be multiple data sets representing the lumen of interest which have been obtained at different times. The clinician will again usually want to directly compare flythroughs of these data sets, e.g., to look for temporal changes in the lumen.

However, with the above described technique for orienting a virtual camera, the camera will adopt an effectively random roll angle about its view vector at locations along the flight path. This means a feature of interest might appear in the top left of a rendered image in a flythrough of one data set, but in the bottom right of a rendered image in a flythrough of another data set, even if the data sets represent the same lumen. This makes it difficult to register and reconcile potential features of interest in one data set with those in another.

This lack of registration between images from different flythroughs increases the difficulty in interpreting the data. Furthermore, it leads to an increased risk that the presence of the same feature in multiple data sets will not be noticed because it appears in different locations in different flythroughs. This can be problematic because features seen in one data set but missed in another will frequently be discounted as not being of interest. In virtual colonoscopy, for example, a feature seen in one data set, but not another, will usually be ignored as being residual fecal matter that has moved between data sets. However, the feature may in fact be a permanent polyp that has been overlooked in one data set, or seen but not recognized as the same feature.

Attempts to address these problems are described by Huang et al. [11]. In one technique, Huang et al., disclose defining a preferred up direction for a virtual camera. During a flythrough, the camera is then oriented about its view direction to align its preferred up direction as far as possible with an up direction in a world coordinate system. However, as Huang et al. explain, this approach still leads to sudden twists and turns which can disorient a user and induce nausea. Huang et al. note that Paik et al. [12] attempt to address this by linking the orientation to one frame to that in a previous frame. However, this again leads to camera orientations which are not reproducible in different data sets. Huang et al. propose an alternative scheme in which a virtual camera is oriented about its roll axis to align with teniae coli structures of the colon. However, a drawback with this approach is that it cannot be performed automatically since a significant amount of clinician input is required to manually identify the teniae coli in the first instance. Automation is generally preferred for medical image data pre-processing since this saves clinician time, both in terms of the clinician having to take part in the pre-processing, and also in terms of the clinician having to wait for the results of the pre-processing before continuing his analysis. Automation can also help improve objectivity and reproducibility in the analysis because a possible source of clinician subjectivity is removed.

Accordingly, there is a need for an improved method of automatically determining a viewpoint orientation for navigating a virtual camera through a biological object with a lumen.

SUMMARY OF THE INVENTION

According to a first aspect of the invention there is provided a method of orienting a virtual camera for rendering a virtual endoscopy image of a lumen in a biological structure represented by a medical image data set, the method comprising: (a) selecting a location from which to render an image; (b) determining an initial orientation for the virtual camera relative to the data set for the selected location based on the geometry of the lumen; (c) determining an offset angle between the initial orientation and a bias direction; and (d) orienting the virtual camera in accordance with a rotation from the initial orientation towards the bias direction by a fractional amount of the offset angle which varies according to the initial orientation.

Thus the method allows images to be rendered from locations along a virtual endoscopy flight path (navigation path) in a way that appears to tend to align the camera with an artificial gravity direction. This helps to provide a user with a more easily interpretable, and less disorienting, virtual endoscopy experience. Furthermore, because the images tend to align with a direction that can be the same in different data sets, flythrough of different data sets representing the same lumen will tend to adopt the same camera orientation when in the same parts of the lumen. This allows for easier comparison of virtual endoscopy flythroughs through different data sets since features which are attached to the lumen wall, e.g. polyps in a virtual colonoscopy, will tend to appear in the same part of corresponding images in different flythroughs. This is because the camera orientation is registered with respect to a selected direction with respect to patient orientation. Furthermore, by orienting the virtual camera in accordance with a rotation from the initial orientation towards the bias direction by a fractional amount of the offset angle which varies according to the initial orientation, a balance between providing an observer with a perception of gravity, and maintaining a preferred view direction so far as the geometry of the lumen is concerned and avoiding potential barrel rolling of the virtual camera can be provided.

In some embodiments, the fractional amount may vary according to the offset angle itself.

For example, the fractional amount may vary so that it is unity if the offset angle is less than a predetermined full-rotation threshold, and otherwise less than unity. Thus the virtual camera can rotate fully to realign from its initial orientation to the bias direction if the offset angle is small (i.e. less than the predetermined full-rotation threshold) so that a full perception of gravity can be provided where this can be done without moving the view direction for the virtual camera from its initially determined orientation by great an amount. The predetermined full-rotation threshold may, for example, be selected from the group consisting of 1°, 2°, 3°, 4°, 5°, 6°, 7°, 8°, 9°, 10°, 11°, 12°, 13°, 14° and 15°.

Furthermore, the fractional amount may be zero if the offset angle is greater than a predetermined no-rotation threshold (which in some cases may be the same as the predetermined full-rotation threshold). This can help to ensure the camera is not reoriented when it would be counter productive to do so. For example, because it would have to move by so much that the view direction would be moved too far from the its initially determined position based on the geometry of the lumen. The predetermined no-rotation threshold may be selected from the group consisting of 15°, 20°, 25°, 30°, 35°, 40°, 45° and 50°, for example.

In some embodiments, the fractional amount may vary between zero and unity if the offset angle is within a predetermined partial-rotation range. For example, in embodiments where the above-referred to predetermined full-rotation threshold and predetermined no-rotation threshold are employed, the predetermined partial-rotation range may run between these thresholds. Alternatively, the predetermined partial-rotation range may span all possible offset angles (0° to 180°). For example, the predetermined partial-rotation range may have lower boundary selected from the group consisting of 0°, 1°, 2°, 3°, 4°, 5°, 6°, 7°, 8°, 9°, 10°, 11°, 12°, 13°, 14° and 15° and an upper boundary selected from the group consisting of 15°, 20°, 25°, 30°, 35°, 40°, 45°, and 50°. The fractional amount may, for example, decrease linearly, or exponentially, with increasing offset angle within the predetermined partial-rotation range. By varying the fractional amount in this way, the user is provided with the perception of an increasing gravitational force as the camera gets closer to being aligned with the bias direction. This has been found to reduce user disorientation.

In other examples, the fractional amount may vary according to an angular separation between a predetermined direction in the data set and a view direction of the virtual camera for the initial orientation.

For example, the data set may comprise voxels arranged along three orthogonal data set axes, and the predetermined direction may be aligned with one of these axes. The choice of predetermined direction therefore defines the perceived direction of gravity. The predetermined direction may thus be a posterior direction in the biological structure. This has been found to provide a readily interpretable fly through. This is because it corresponds to aligning the virtual camera with gravity for a patient lying on their back, which is a common pose for medical examinations. Any other direction could be used.

In cases where the fractional amount varies according to an angular separation between a predetermined direction in the data set and a view direction of the virtual camera for the initial orientation, the fractional amount may be zero if the angular separation is less than a predetermined no-rotation threshold. This helps to avoid alarming barrel rolls that may otherwise occur as a flight path changes direction about the perceived vertical which is aligned with the predetermined direction (whether is heading "up" or "down"). The predetermined no-rotation threshold may be selected from the group consisting of 1°, 2°, 3°, 4°, 5°, 6°, 7°, 8°, 9°, 10°, 11°, 12°, 13°, 14°, 15°, 16°, 17°, 18°, 19° and 20° (it being understood that the angular separation may be measured from "up" or "down" along the predetermined direction).

Furthermore, the fractional amount may be unity if the angular separation is greater than a predetermined full-rotation threshold. For example, the predetermined full-rotation threshold may be selected from the group consisting of 15°, 20°, 25°, 30°, 35°, 40°, 45° and 50°. This ensures the full effects of the perceived virtual gravity can be provided when there is little risk of barrel roll because the flight path is significantly far from being aimed directly "up" or "down".

In some embodiments, the fractional amount may vary between zero and unity if the angular separation is within a predetermined partial-rotation range. For example, in embodiments where the above-mentioned predetermined full-rotation threshold and predetermined no-rotation threshold for the angular separation are employed, the predetermined partial-rotation range may run between these thresholds. Alternatively, the predetermined partial-rotation range may span all possible angular separations, i.e., 0° to 90° (since angular separation can be measured from either "up" of "down" along the predetermined direction, it is only necessary to consider this range). For example, the predetermined partial-rotation range may have lower boundary selected from the group consisting of 0°, 1°, 2°, 3°, 4°, 5°, 6°, 7°, 8°, 9°, 10°, 11°, 12°, 13°, 14°, 15°, 16°, 17°, 18°, 19° and 20°, and an upper boundary selected from the group consisting of 15°, 20°, 25°, 30°, 35°, 40°, 45°, and 50°. The fractional amount may, for example, increase linearly, or exponentially, with increasing angular separation within the predetermined partial-rotation range. This has been found to assist user orientation.

The virtual camera may be orientable about orthogonal roll (view), pitch (right) and yaw (down) axes, the roll axis being aligned with a view direction for the virtual camera, and the bias direction may be a projection of a predetermined direction in the data set onto a plane containing the roll (right) and yaw (down) axes for the initial orientation. This provides the perception of a camera that changes its pitch to align its yaw (down) axis with gravity.

Furthermore, the bias direction may also comprise a projection of a predetermined direction in the data set onto a plane containing the pitch and yaw axes for the initial orientation. This provides the perception of a camera that changes its roll to align its yaw (down) axis with gravity.

Furthermore still, in some, if not most, embodiments there may be two bias directions, namely a first bias direction that is a projection of a predetermined direction in the data set onto a plane containing the roll (right) and yaw (down) axes for the initial orientation, and a second bias direction that is a projection of the same predetermined direction in the data set onto a plane containing the pitch and yaw axes for the initial orientation. This provides the perception of a camera that changes its pitch and roll to align its yaw (down) axis with gravity (i.e. the predetermined direction).

The method may also include determining a desired orientation for the virtual camera relative to the data set for the selected location based on the geometry of the lumen, determining a relocation angle between the desired orientation of the virtual camera and a previous orientation of the virtual camera, and determining the initial orientation of the virtual camera to be the desired orientation if the relocation angle is greater than a relocation angle threshold, and otherwise maintaining the previous orientation as the initial orientation. This has been found to help increase the perceived smoothness of a flythrough. The relocation angle threshold may, for example, be selected from the group consisting of 1°, 2°, 3°, 4°, 5°, 6°, 7°, 8°, 9° and 10°.

The method may further comprise translating the virtual camera from the selected location on the flight path to a new location, wherein the new location is determined in accordance with the geometry of the lumen and the orientation of the camera after the rotation from the initial orientation towards the bias direction by a fractional amount of the offset angle which varies according to the initial orientation. Thus a modified flight path may be provided which takes account of the reorientation of the camera at locations on a flight path.

The method may also comprise rendering an image for the selected location and orientation of the virtual camera. And, furthermore still, may comprise displaying the rendered image on a display. Alternatively, or additionally, the rendered image may be stored on a storage medium, or in a memory, for later display.

Multiple images may be rendered in this way from a series of selected locations is along a navigation path (flight path) through a lumen, and displayed to a user to provide a virtual endoscopy sequence, e.g. a virtual colonoscopy sequence of a lumen.

According to another aspect of the invention there is provided a computer program product comprising machine readable instructions for implementing the method of the first aspect of the invention.

The computer program product may comprise a computer program on a carrier medium, for example a storage medium or a transmissions medium.

According to another aspect of the invention there is provided a computer configured to perform the method of the first aspect of the invention.

According to still another aspect of the invention there is provided an apparatus for implementing the method of the first aspect of the invention. For example, the apparatus may comprise a suitably configured application specific integrated circuit (ASIC), a field programmable gate array (FGPA), or an arrangement of discrete components for executing the method.

BRIEF DESCRIPTION OF THE DRAWINGS

For a better understanding of the invention and to show how the same may be carried into effect reference is now made by way of example to the accompanying drawings in which.

DETAILED DESCRIPTION

Virtual endoscopy is often used in the study of the colon. In this context, virtual endoscopy is often referred to as virtual colonoscopy. Embodiments of the invention will hereafter be described by way of example in the specific context of virtual colonoscopy. However, it will be understood that embodiments of the invention may equally be employed in other applications of virtual endoscopy, for example in virtual angiography, virtual bronchoscopy, and also in computer simulated flythroughs of biological structures which are not normally the subject of conventional endoscopy procedures.

Figure 1:
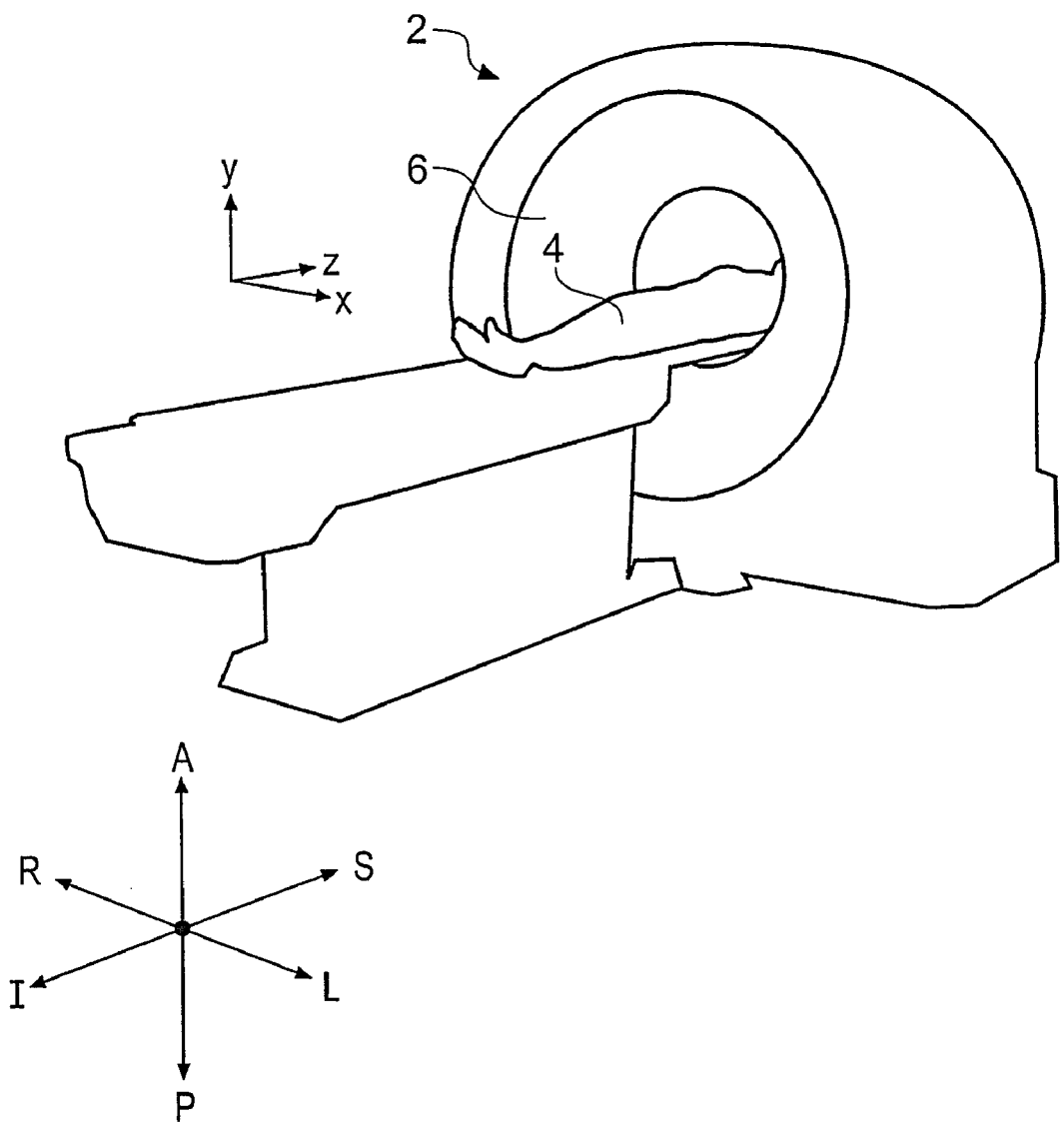
FIG. 1 schematically shows a generic x-ray CT scanner for generating volume data sets for processing in accordance with embodiments of the invention.

FIG. 1 is a schematic perspective view of a generic x-ray CT scanner 2 for obtaining a three-dimensional (3D) scan of a patient 4 to provide data suitable for virtual colonoscopy according to an embodiment of the invention. The patient's abdominal region is placed within a circular opening 6 of the CT scanner 2 and a series of x-ray images are taken from directions around the patient. The raw image data are combined using tomographic techniques to produce a volume data set. The volume data set comprises a collection of voxels. Conventionally, the volume data set is aligned with transverse, sagittal and coronal planes. Thus a Cartesian coordinate system may be defined relative to the patient in which the xy-axes are in a transverse plane, the xz-axes are in a coronal plane and the yz-axes are in a sagittal plane. The conventional orientations for the x, y and z-axes relative to the patient are schematically shown to the top left of FIG. 1. In this orientation the z-axis increases from the patient's feet to his head. (i.e. inferior to superior), the x-axis increases from the patient's left to his right, and the y-axis increases from the patient's rear to his front (posterior to anterior). The superior (S), inferior (I), left (L), right (R), anterior (A) and posterior (P) directions are shown in the lower left of the figure. The orientations of these directions are relative to the patient, and not the CT scanner. That is to say, if the patient orientation shown in FIG. 1 were to be different, so would the superior, inferior, left, right, anterior and posterior directions in the figure. For example, if the patient were lying on his front rather than back (prone rather than supine) the anterior and posterior directions would be reversed, as would the left and right directions. The superior and inferior directions would, however, remain the same in this case.

Each voxel in the volume data set has a signal value associated with a physical parameter of the corresponding portion of the scanned object. For example, for a CT scan, the signal value (or image parameter) for a given voxel is a measure of how much the corresponding portion of the patient's body absorbs x-rays. The image parameter may thus be referred to as radiodensity. Radiodensity is conventionally calibrated according to the Hounsfield scale. The Hounsfield scale is defined such that air has a radiodensity of −1000 HU Hounsfield units) and water has a radiodensity of 0 HU. Typical radiodensity values for other materials are −50 HU for body fat, +40 HU for soft tissue, such as muscle, and +1000 HU for bone.

To obtain data suitable for virtual colonoscopy the patient will normally have undergone a colonic lavage and sufflation procedure prior to scanning. This means, at least so far as possible, the colon is full of gas and free of obstructions while the image data are acquired. This ensures the extent of the colon is readily apparent in the medical image volume data set. For example, for a data set from a CT scanner such as shown in FIG. 1, the colon will be associated with voxels having low radiodensities, for example less than around −600 HU or so. This is because the gas in the colon is a relatively poor absorber of x-rays. The colonic walls and surrounding body tissue, on the other hand, will have greater radiodensities, for example closer to 0 HU, or denser.

Figure 2:
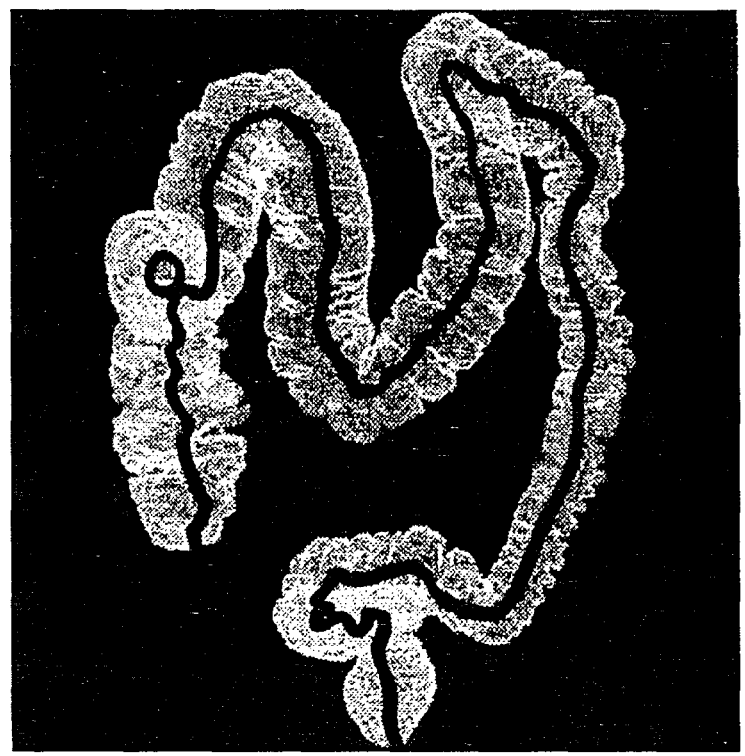
FIG. 2 schematically shows a 2D image rendered from a 3D volume data set of the kind suitable for virtual colonoscopy.
Figure 3:
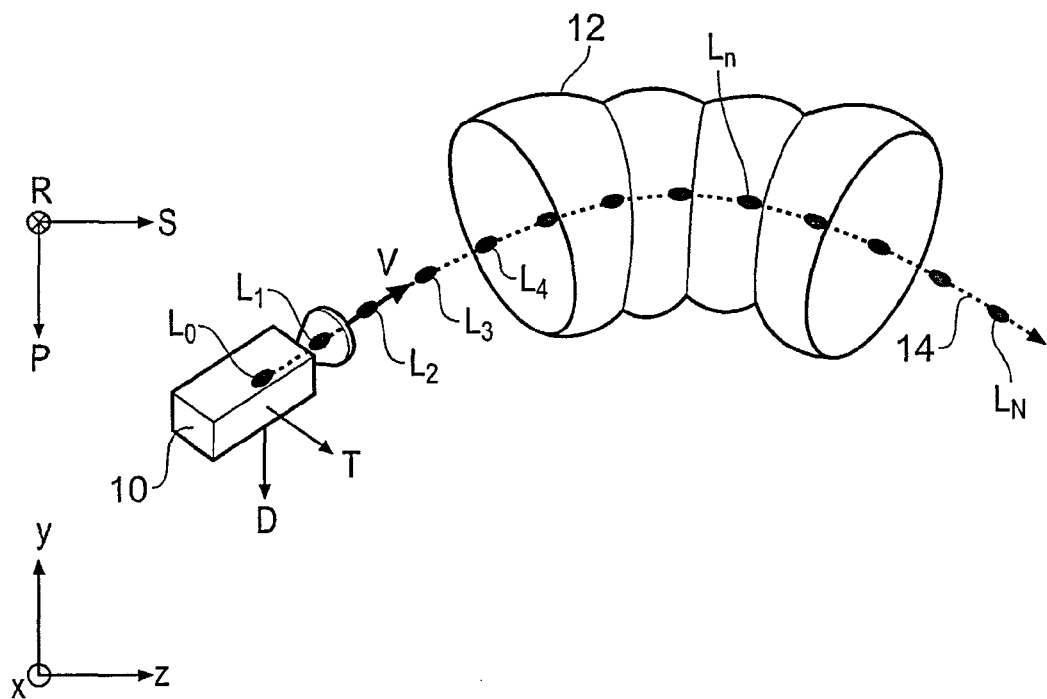
FIG. 3 schematically shows a perspective view of a virtual camera viewing a section of virtual colon from two locations according to an embodiment of the invention.

FIG. 2 schematically shows a 2D image rendered from a 3D volume data set of the kind suitable for virtual colonoscopy. The 2D image in FIG. 3 is rendered so that voxels corresponding to the boundary between gas inside the sufflated colon and the surrounding body tissue are rendered semi-opaque, and all other voxels are rendered transparent. Thus the colon appears as if it were a translucent structure inside an otherwise invisible patient. The view shown in FIG. 2 is taken from a direction which is almost directly in front of the patient (i.e. a view along the posterior-anterior axis and looking in the posterior direction). The patient is close to upright in the image. Thus, the patient's rectum is apparent at the bottom-centre of the image.

The components of the digestive tract apparent in FIG. 2 include the cecum, ascending colon, transverse colon, descending colon, sigmoid colon, rectum and anus. In a typical colonoscopy screening procedure (whether real or virtual), the clinician will normally start at the anus and view the digestive tract along a path passing through many, if not all, of the rectum, sigmoid colon, descending, transverse and ascending colon, and cecum. For simplicity, all the parts of a patient's anatomy typically viewed during a colonoscopy procedure will be collectively be referred to here as the colon.

Thus the term should be understood accordingly to include at least these anatomical parts unless the context demands otherwise, it being understood that this meaning may not correspond exactly with a strict medical definition of the term.

Also shown in FIG. 2 is a predetermined flight path (navigation path) for a virtual camera to follow in a virtual colonoscopy procedure based on the volume data set. The flight path is represented in the figure as a heavy black line running through the colon. The flight path may be determined using any conventional technique, for example any of those referred to above [1, 2, 3, 4, 5, 6, 7]. In accordance with an embodiment of the invention, images for a virtual colonoscopy fly through of the colon are obtained by rendering images from different locations along the flight path and for different viewing directions.

FIG. 3 schematically shows in perspective view a virtual camera 10 viewing a section of colon 12 seen FIG. 2 according to an embodiment of the invention. Also shown in FIG. 3 (as a dotted line) is a corresponding section of the predetermined flight path 14, and locations $L_0, L_1, \ldots L_n, \ldots$, from which images are to be rendered for the flythrough. As noted above, the flight path 14 and rendering locations $L_0, L_1, \ldots L_n, \ldots L_N$, may be determined using conventional techniques. Here it is assumed that the rendering locations $L_n$ are separated from one another along the flight path 14 by 1 mm spacings.

The orientations of the posterior (P), superior (S), and right (R) directions of the volume data set are shown in the top left of the figure. (The anterior, inferior, and left directions are respectively opposite to these directions.) The plane of the figure is therefore parallel to a sagittal slice in the data set. Thus the section of colon 12 extends substantially along the inferior-superior direction, but is curved slightly such that in moving from the inferior to the superior, the colon starts in an upwards and towards the right of the patient direction, and ends in a downwards and towards the left of the patient direction.

The concept of a virtual camera, such as shown in FIG. 3, is commonly used in medical imaging to define a view point from which images are to be rendered. Six coordinates are required to fully define a view point for a rendered image. Namely three spatial coordinates and three angular coordinates.

The spatial coordinates locate the camera within the volume data set, i.e. they define the rendering locations $L_n$ in the x-, y- and z-Cartesian coordinate system shown in FIG. 1 (relative to an arbitrary origin). The x-, y-, z-coordinate system is conventionally registered with the superior, inferior, left, right, anterior and posterior directions, again as shown in FIG. 1. The orientations of the x-, y- and z-directions are also shown to the bottom left of FIG. 3.

The angular coordinates of the virtual camera define its orientation about the respective rendering locations $L_n$ for the rendered images, i.e. which way the camera is looking, and which way is up in the rendered image. The orientation of the camera in the data set may be defined by the directions of three orthogonal axes centred on (and moving with) the virtual camera. Thus changes in the orientation of the camera may be defined by angles of rotation about these three orthogonal axes. These axes are shown in FIG. 3 and comprise a view axis V, a down axis D and a right axis T. The view axis, or view vector, V defines the direction the virtual camera is looking, and corresponds with the centre of a rendered image. The down axis, or down vector, D is orthogonal to the view vector V. The orientation of the down vector D about the view vector may be arbitrarily selected in the first instance, but is then preserved (i.e. it moves with changes in the camera orientation). The right axis, or right vector, T is orthogonal to both the view vector V and the down vector D. Referring to the conventional aeronautical coordinate system, the view vector may also be referred to as a roll axis, the down vector may also be referred to as a yaw axis, and the right axis may also be referred to a pitch axis. Thus rotation of the virtual camera about the view vector V may be referred to as roll, rotation of the virtual camera about the down vector D may be referred to as yaw, and rotation of the virtual camera about the right vector T may be referred to as pitch.

Figure 4:
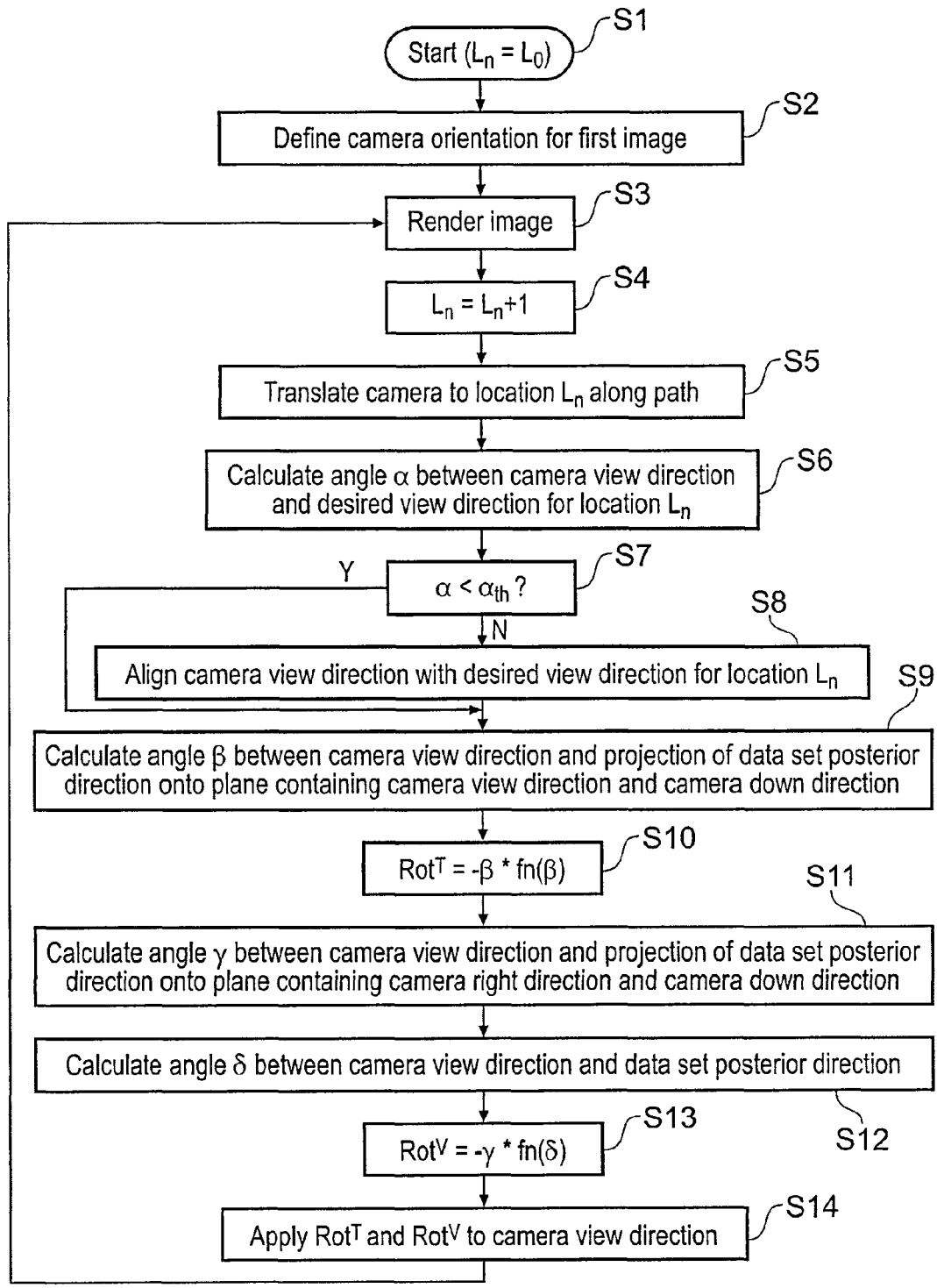
FIG. 4 is a flow chart schematically showing a method of determining a viewpoint for navigating a virtual camera through a colon according to an embodiment of the invention.

FIG. 4 is a flow chart schematically showing a method of orienting a virtual camera at rendering locations $L_n$ along the flight path 14 through the colon 12 shown in FIGS. 2 and 3 according to an embodiment of the invention. The method may be executed on a suitably programmed general purpose computer, for example. Prior to the processing shown in FIG. 4, it is assumed that a suitable data set has been obtained for processing, the lumen of interest has been segmented, and a desired flight path and series of rendering locations have been determined. These steps may be performed using conventional techniques. For example, the data set may be obtained by retrieval from storage on a hard disk drive of a computer system configured to perform the method, retrieved over a network, for example a Picture Archiving and Communication System (PACS) network, or obtained directly from an imaging modality, for example the CT scanner shown in FIG. 1, immediately following a scan of a patient. The segmentation for classifying voxels in the data set according to tissue type/anatomical feature may be done using automatic segmentation schemes such as described by Wyatt et al. [12] or Frimmel et al. [13], for example, or any other scheme. The flight path and rendering locations may be determined using any of the techniques previously referred to [1, 2, 3, 4, 5, 6, 7], or any other scheme.

In the following description of the method shown in FIG. 4, there are numerous references to translations, rotations, and calculating angles between vectors and directions etc., and it will be understood that these can be determined and applied as appropriate in accordance with conventional mathematical processing techniques, such as vector/matrix algebra or algorithmic equivalents. Furthermore, it will be appreciated that the magnitudes of the various vectors referred to in the following description are not generally significant, and thus references to vectors may be taken as reference to unit vectors, unless the context demands otherwise.

Processing starts at step S1 where a rendering location parameter $L_n$ is set to $L_0$.

In step S2, a camera orientation for the first image (i.e. the image to be rendered from location $L_0$) on the flight path 14 is defined. This involves defining a pointing direction for the virtual camera's view vector V, and a roll angle for the virtual camera about its view vector V. The pointing direction may be determined from the geometry of the lumen according to any known technique, and furthermore, the same technique will in general be used to define initially desired view directions for each location on the flight path. In this example, the view vector V is aligned so that it points to a location a fixed distance ahead on the flight path, and in particular a distance that is four steps ahead of the current location. Thus the direction of the view vector is defined by a line connecting location $L_0$ to $L_4$. Because the flight path is not tightly curved between $L_0$ and $L_4$ in this example, the view direction is closely aligned with the flight path. Any other of the many well known techniques for defining a pointing direction for a virtual camera based on the geometry of the lumen may also be used to define the direction of the view vector. For example the pointing direction may be taken to be the direction which is tangential to the flight path at the current camera location, or selected so that the pointing direction grazes the inside of the nearest turn in the lumen ahead of the camera, or strikes the farthest point of the lumen visible from the current camera location. The roll of the virtual camera about the pointing direction for the rendering of the first image is selected so that the camera's down vector aligns as closely as possible with a predetermined direction in the data set. Here the predetermined direction is chosen to be the posterior direction.

(In general, the orientation initially defined in step S2 for the first image will be modified by processing similar to that set out in steps S9 and S10 discussed further below. However, for simplicity this aspect of the processing is not described in connection with this stage of the method shown in FIG. 4).

In step S3, an image for location $L_0$ is rendered from the data set for the camera orientation defined in step S2. The image may be rendered in any conventional manner using rendering parameters selected according to the desired appearance of the lumen of interest (here the colon) in the virtual endoscopy flythrough to be displayed. The camera orientation defined in step S2 means that the posterior-anterior directions in the data set appears vertical in the rendered image, with the posterior towards the bottom. This gives the impression that the patient is lying on his back (regardless of the patient's actual orientation when the data were acquired), with the virtual camera's orientation about the view axis aligned with gravity for this orientation (i.e. the camera down vector is as closely aligned with posterior direction as possible).

In step S4, the rendering location parameter $L_n$ is incremented by 1.

In step S5, the virtual camera is translated from its current location on the flight path to the next location $L_n$ (i.e. from $L_0$ to $L_1$ for this first iteration through step S5).

In step S6, a desired view direction for the virtual camera at the new location $L_n$ is determined based on the geometry of the lumen. As noted above, the desired view direction at each location may be determined according to conventional techniques, and in this example is determined so that the desired camera view direction is towards a location on the flight path that is four steps ahead of the camera's current location.

Figure 5:
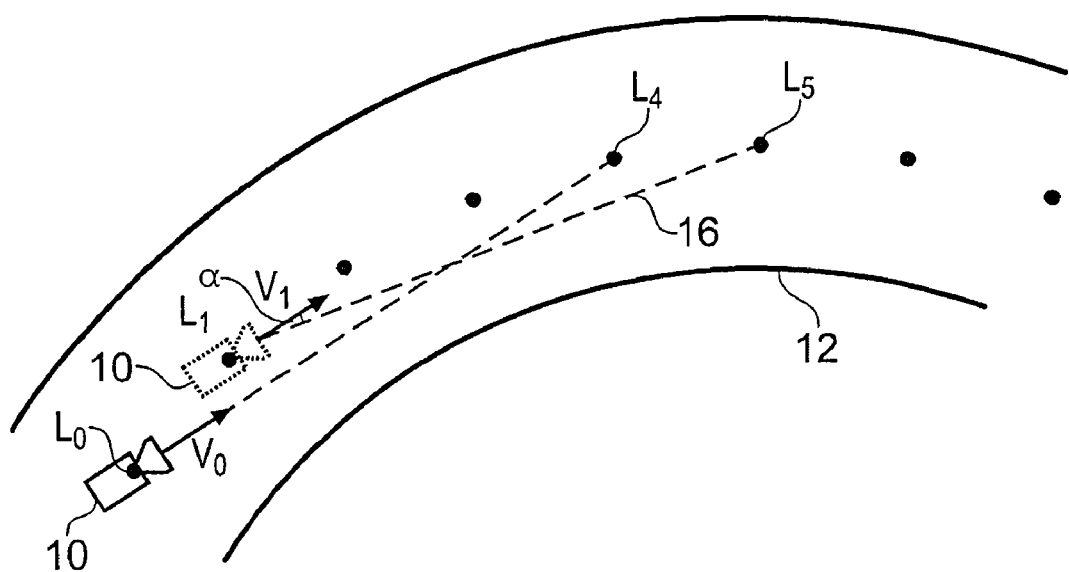
FIG. 5 schematically shows a section view of a virtual camera viewing a virtual colon according to an embodiment of the invention.

FIG. 5 is a schematic section view of the colon 12 taken in an arbitrary plane and showing the virtual camera 10 at two locations. Namely at location $L_0$ (in solid line) and location $L_1$ (in dotted line). The vector marked $V_0$ corresponds with the view direction for the camera defined at step S2 for the first image (i.e. in this case pointing at location $L_4$). The vector marked $V_1$ corresponds with the view direction for the camera after it has been translated to location $L_1$ along the flight path in step S5. The dashed line identified by reference, numeral 16 corresponds with the desired view direction for the camera at, location $L_1$ (i.e. in this case pointing at location $L_5$). The angle α between $V_1$ and the dashed line identified by reference numeral 16 is determined, e.g. by establishing the inner product of unit vectors aligned with $V_1$ and the dashed line identified by reference numeral 16. The calculated angle α is referred to here as the relocation angle for location $L_n$.

In step S7, the relocation angle α is compared with a predetermined relocation angle threshold $α_{th}$. In this embodiment the relocation angle threshold $α_{th}$ is 3 degrees or so. If the relocation angle α is less than the relocation angle threshold $α_{th}$, processing follows the Y branch from step S7 to S9, thereby bypassing step S8. If the relocation angle α is not less than the relocation angle threshold $α_{th}$, processing follows the N branch from step S7 to S8.

In step S8, the virtual camera is rotated by the relocation angle α so that the camera's view direction is aligned with the desired view direction for the present location (i.e. in this case such that the camera view vector is pointing at location $L_{n+4}$).

The purpose of bypassing step S8 if the relocation, angle α is less than the relocation angle threshold $α_{th}$ is to provide what an observer, e.g. clinician, will perceive as a smoother flight along the flight path. The inventors have found that if only a small adjustment is necessary to re-align the camera view vector preserved from the previous location on the flight path with the desired view direction after translation to the new location at step S5, a smoother, less jerky, fly through can, be obtained if step S8 is not performed. However, if a larger adjustment is necessary (e.g. the relocation angle α is not less than the relocation angle threshold $α_{th}$), it is better to perform step S8 so that the camera does not start off pointing too far from the desired direction at the new location.

Thus prior to step S9, an initial orientation for the virtual camera relative to the data set for the present location is provided which is based on the geometry of the lumen. In the event that the relocation angle α was found to be less than the relocation angle threshold $α_{th}$ in step S7, the initial orientation corresponds with that preserved from the previous location during the translation at step S5. If, on the other hand, the relocation angle α was found not to be less than the relocation angle threshold $α_{th}$ at step S7, the initial orientation will correspond with the desired orientation at the current location, i.e. in the present case corresponding to looking four steps ahead along the flight path. (It will be appreciated that other distances could be used, for example, 1, 2, 3, 4, 5, 6, 7, 8, or more steps may be used. The distance may also be defined in physical units, e.g. 5 mm, 10 mm, 15 mm, 20 mm, 25 mm, or more.)

Figure 6:
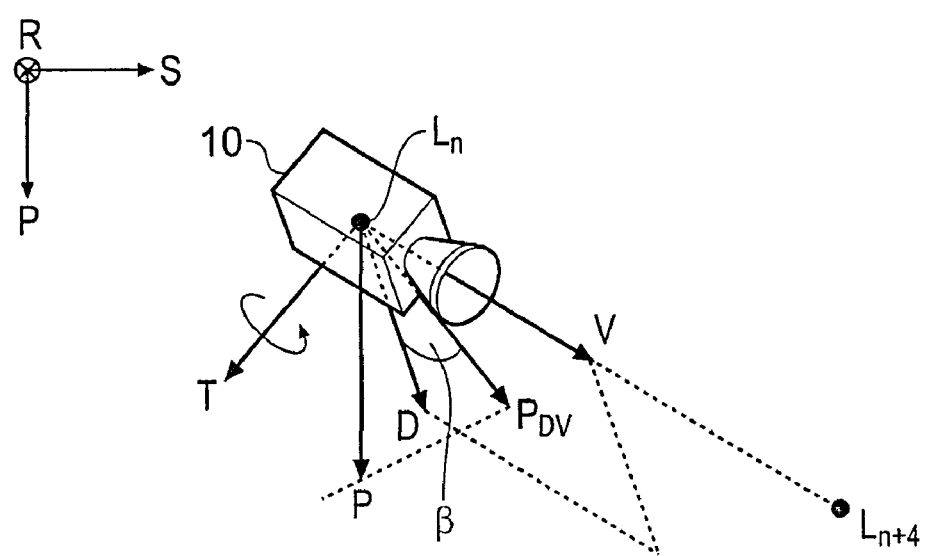
FIG. 6 schematically shows the orientation of a virtual camera at one stage of the processing shown in FIG. 4.

FIG. 6 schematically shows the virtual camera 10 at a location $L_n$ on the flight path prior to step S9 of the processing shown in FIG. 4. The camera is thus shown in its initial orientation for location $L_n$. It can be seen here that the view vector V is directed towards location $L_{n+4}$, and so the initial orientation for location $L_n$ corresponds with the desired view direction for this location. That is to say, the camera is at a location for which step S8 was considered necessary, i.e. the relocation angle was found to be greater than the relocation angle threshold. (Or in the alternative it may be the special case that the relocation angle determined in step S6 was zero). Also shown in FIG. 6 are the virtual camera's view vector V, right vector T and down vector D. In addition, a posterior vector P is shown. The posterior vector P is a vector running parallel to, and in the same direction as, the posterior direction in the data set, and passing through location $L_n$ (i.e. the centre of the virtual camera and the intersection of its view vector V, right vector T and down vector D). One further vector is shown in FIG. 6 and is labelled $P_{DV}$. Vector $P_{DV}$ corresponds to the projection of the posterior vector P onto the plane containing the virtual camera's view vector V and down vector D. This projection vector may be considered to define a bias direction for pitch since processing in accordance with the method shown in FIG. 4 acts to bias the orientation of the virtual camera about its pitch axis such that the camera down vector D tends towards alignment with the projection of the posterior vector P onto the plane containing the camera view vector V and down vector D.

Accordingly, in step S9, an offset angle β is determined. This is the angle between the camera down vector D in its initial orientation and projection vector $P_{DV}$.

In step S10, a rotation angle $Rot^T$ about the virtual camera right axis T is determined (i.e. $Rot^T$ is a pitch angle). $Rot^T$ is an angle through which the camera will be rotated about its right vector at a later stage of the processing. The direction of the rotation is from the down vector D towards the projection vector $P_{DV}$. Thus for the orientation shown in FIG. 6, the direction of the rotation is as indicated by the arrow around the camera right vector T. The reason for rotating the camera about the right vector in this way is so that the camera tends to align its down vector with the posterior direction in the data set. The inventors have found that this leads to a more settling and less disorienting flythrough for a user compared to previous techniques. This is because rotation of the down vector D towards the projection Vector $P_{DV}$ gives the user a perception that the camera is subject to a virtual gravity force directed towards the posterior of the data set. This has been found to help to orient the user.

However, it is important that $Rot^T$ is not simply chosen to rotate the camera about its right vector by an amount $-\beta$ such that its down vector D is moved fully to coincide with the projection vector $P_{DV}$ regardless of the value of $\beta$. This is because rotating the camera about its right axis to reorient its down vector D towards the projection vector $P_{DV}$ also necessarily reorients the view Vector V. This means if $Rot^T$ were simply taken to be $-\beta$, at large values of p the rotation of the view direction V away from the initial orientation determined for the present position would be too great, and the rotation to align the camera down vector D with the virtual gravity direction would be counter productive. This is illustrated by FIGS. 7 and 8.

Figure 7:
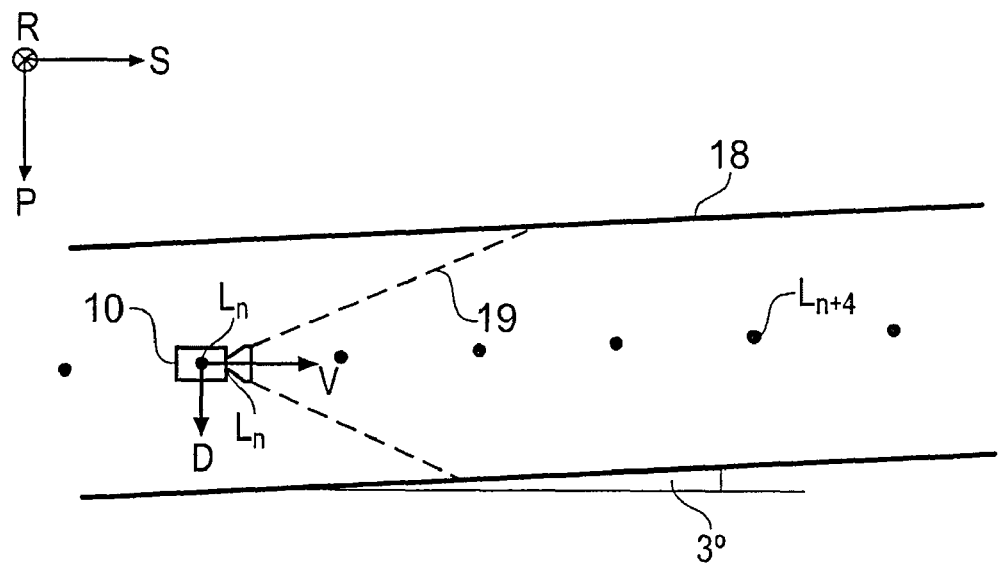
FIG. 7 schematically shows a section view of a virtual camera viewing a virtual colon according to an embodiment of the invention.

FIG. 7 schematically shows in section view a virtual camera 10 at a location $L_n$ along a flight path in a portion of colon 18. The field of view 19 of the virtual camera is indicated by the dotted cone 19. The field of view 19 is defined by the rendering parameters of the rendering technique being employed in the usual way. The view in FIG. 7 is taken in a sagittal plane of the data set. The orientations of the posterior (P), superior (S), and right (R) directions of the volume data set are shown in the top left of the figure. (The anterior, inferior, and left directions are respectively opposite to these directions). For ease of explanation, the section of colon 18 is considered to be straight and of uniform cross-section. Furthermore, the section of colon is taken to have an axis of extent that runs upwards from inferior to superior at an angle of 3° to a coronal plane. For such a colon, at least for typical flight path generation techniques, the flight path (and hence locations $L_n$ and $L_{n+4}$) will also be in the plane of the figure. Accordingly, the view direction associated with the initial orientation of the virtual camera determined for location $L_n$ will be within the plane of the figure, and furthermore will be angled upwards (from inferior to superior) by 3°. For simplicity, the roll of the virtual camera about the view vector in the initial orientation for location $L_n$ is taken to be such that the down vector D is also in the plane of the figure. Thus the right vector T (not shown in FIG. 7) extends perpendicularly out of the plane of the figure.

The virtual camera is shown in FIG. 7 as if it had been rotated about its right vector T by an amount $Rot^T$ equal in size (though opposite in direction) to the angle $\beta$ determined at step S9 of the processing shown in FIG. 4. For the portion of colon 18 and corresponding flight path shown in FIG. 7, $\beta$ is 3°. In this case, the rotation of the virtual camera about its right vector T by 3° provides the user with a perception of virtual gravity drawing the camera down vector towards the posterior direction in the data set, while maintaining a good view of the colon in the rendered image from this location (as defined by the field of view 19).

Figure 8:
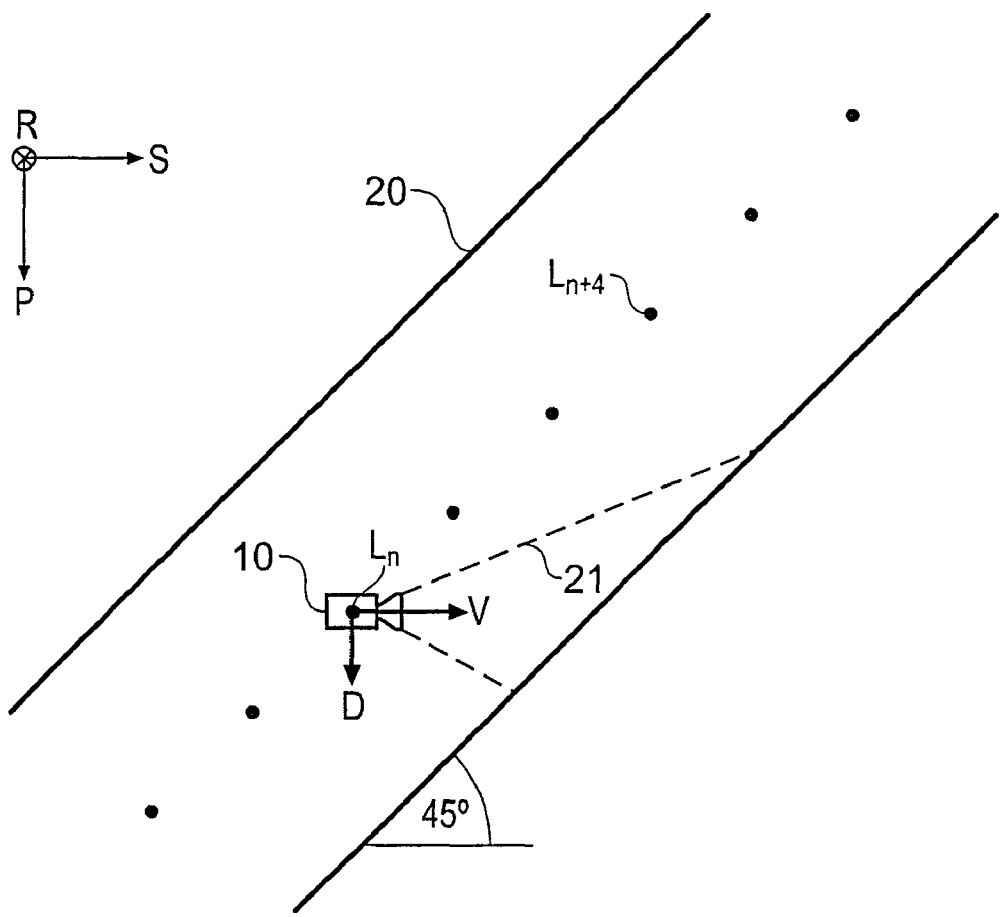
FIG. 8 schematically shows another section view of a virtual camera viewing a virtual colon.

FIG. 8 is similar to, and will be understood from FIG. 7. However, whereas in FIG. 7 the section of colon 18 is inclined at only 3° to the coronal plane, FIG. 8 shows a section of colon 20 inclined at an angle of 45° to the coronal plane. As with FIG. 7, the virtual camera 10 in. FIG. 8 is shown as if it had been rotated about its right vector r by an amount $Rot^T$ equal in size (though opposite in direction) to the angle $\beta$ determined at step S9 of the processing shown in FIG. 4. For the portion of colon 20 and corresponding flight path shown in FIG. 8, $\beta$ is 45°. In this case, the rotation of the virtual camera about its right vector T by 45° again provides the user with a perception of virtual gravity drawing the camera down vector D towards the posterior direction in the data set. However, it does so at the expense of providing a significantly degraded view for the rendered image. This is because the field of view 21 for the virtual camera in FIG. 8 is directed too far from the initially determined direction (i.e. the direction towards the location $L_{n+1}$), and is directed too much towards one side of the lumen wall.

This demonstrates why the virtual camera should not simply be rotated about its right vector by an amount $-\beta$ to align its down vector D with the projection vector $P_{DV}$ regardless of the magnitude of $\beta$. Accordingly, the inventors have appreciated that in some circumstances improved results can be achieved if $Rot^T$ is calculated as a fractional amount of $\beta$, where the fractional amount depends on $\beta$. That is to say where $Rot^T = -\beta * fn(\beta)$, where $fn(\beta)$ is a function that varies between zero and unity according to $\beta$.

Figure 9:
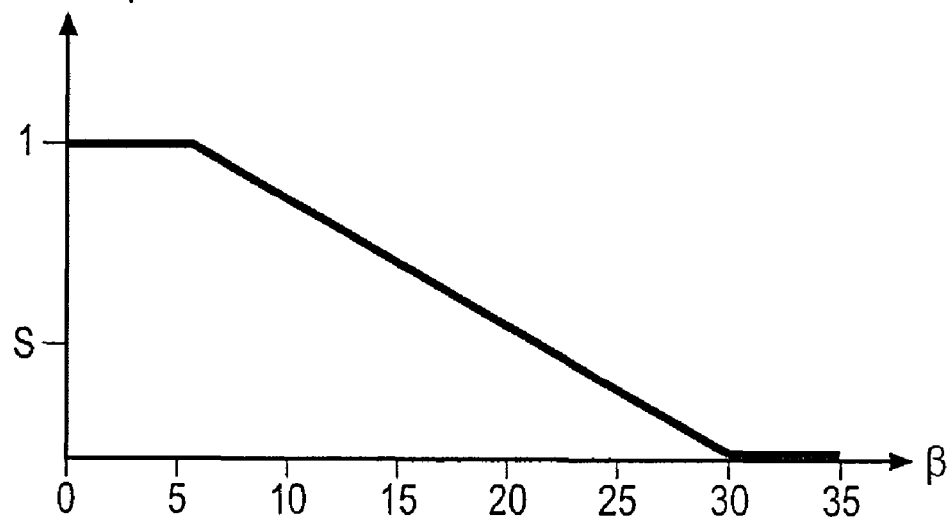
FIG. 9 is a graph schematically showing the ratio of a rotation in pitch angle applied to a virtual camera to the pitch angle as a function of the pitch angle according to an embodiment of the invention.

FIG. 9 is a graph schematically showing a form for $fn(\beta)$ which may be used at step S10 to calculate $Rot^T$. The inventors have found this form of $fn(\beta)$ provides a good balance between providing a user with a perception of virtual gravity through rotation of the virtual camera about its right vector, while maintaining a reasonable view of the colon ahead in rendered images. For values of $\beta$ less than a predetermined full-rotation threshold, in this case 5°, $fn(\beta)$ is set to unity (that is to say $Rot^T = -\beta$). As shown in FIG. 7, setting $Rot^T$ to be equal and opposite to $\beta$ is not problematic for relatively small values of $\beta$. For values of $\beta$ greater than a predetermined no-rotation threshold, in this case 30°, $fn(\beta)$ is set to zero (that is to say $Rot^T = 0$). This is because the inventors have found that it can be counter productive to attempt any reorientation of the camera for values of $\beta$ on this order and higher because of the detrimental effects on view direction. Between the full-rotation threshold and the no-rotation threshold (i.e. for around $5 < \beta < 30$), $fn(\beta)$ decreases, in this case linearly, from unity to zero with increasing $\beta$. Other variations, e.g. an exponential variation, could also be used in this range.

The inventors have found that by varying the value of $fn(\beta)$ (and hence $Rot^T$) in the kind of way shown in FIG. 9 (i.e. in a way that depends on the initial orientation of the camera), a natural looking flythrough can be obtained which balances the advantages of providing a perception of gravity, and the advantages of maintaining the most appropriate view direction based on the geometry of the colon lumen.

Figure 10:
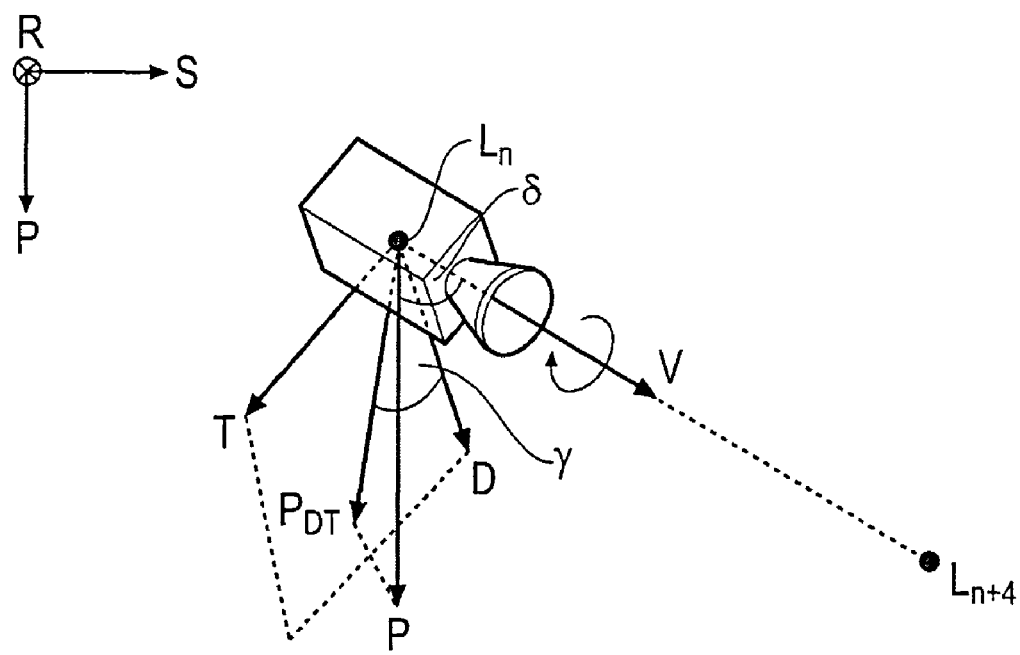
FIG. 10 schematically shows the orientation of a virtual camera in the same position as in FIG. 7, but at another stage of the processing shown in FIG. 4.

FIG. 10 schematically shows the virtual camera 10 at location $L_n$ on the flight path prior to step S11 of the processing shown in FIG. 4. Although it is noted in this embodiment the rotation angle $Rot^V$ for the camera about its right axis determined at step S10 has not yet been applied. Accordingly, the camera orientation in FIG. 10 is the same as that in FIG. 6. The camera is thus still shown in its initial orientation for location $L_n$. As with FIG. 6, also shown in FIG. 10 are the virtual camera's view vector V, right vector T and down vector D. The posterior vector P is also shown again. However, $P_{DV}$ is not shown in FIG. 10, and a different projection vector $P_{DT}$ is shown instead. Projection vector $P_{DT}$ corresponds to the projection of the posterior vector P onto the plane containing the virtual camera's right vector T and down vector D. This projection vector may be considered to define a bias direction for roll since processing in accordance with the method shown in FIG. 4 acts to bias the orientation of the virtual camera about its roll axis such that the camera down vector D tends towards alignment with the projection of the posterior vector P onto the plane containing the camera right vector T and down vector D.

In step S11, an offset angle γ is determined. This is the angle between the camera down vector D in its initial orientation and projection vector $P_{DT}$.

In step S12, an angular separation δ is determined between the camera view vector V in its initial orientation and the posterior direction P. This is a measure of how close the virtual camera is to looking directly along the posterior direction. Thus if γ=0°, the view direction is aligned with the posterior direction, if γ=90°, the view direction is perpendicular to the posterior direction, and if γ=180°, the view direction is aligned with the anterior direction.

In step S13, a rotation angle $Rot^V$ about the virtual camera view vector V is determined (i.e. $Rot^V$ is a roll angle). $Rot^V$ is an angle through which the camera will be rotated about its right vector at a later stage of the processing. The direction of the rotation is from the down vector D towards the projection vector $P_{DT}$. Thus for the orientation shown in FIG. 10, the direction of the rotation is as indicated by the arrow around the camera view vector V. The reason for rotating the camera about the view vector in this way is so that the camera tends to align its down vector with the posterior direction in the data set. As noted above in relation to the rotation about the right axis determined in steps S9 and S10, the inventors have found that this leads to a more settling and less disorienting flythrough for a user. Again this is because rotation of the down vector D towards the projection vector $P_{DT}$ gives the user a perception that the camera is subject to a virtual gravity force directed towards the posterior of the data set.

As described above in relation to step S10, when determining an appropriate rotation $Rot^T$ about the right axis, there is an issue with balancing the provision of a perception of gravity, and maintaining the most appropriate view direction based on the geometry of the colon lumen. However, this issue does not arise when determining an appropriate rotation $Rot^V$ about the virtual camera view vector V. This is because rotations about this axis do not significantly affect what features of the lumen fall within the field of view of the virtual camera, they only affect where in the rendered image they appear.

However, it is nonetheless still important that $Rot^V$ is not simply chosen to rotate the camera about its view vector by an amount −γ such that its down vector D is moved fully to coincide with the projection vector $P_{DT}$, irrespective of the camera orientation in the data set. This is because when the camera is oriented such that its view direction is close to the anterior-posterior direction, i.e. close to being directed directly up or directly down relative to the perceived direction of gravity, a relatively small change in the direction of extent of the lumen from one rendering location $L_n$ to the next rendering location $L_{n+1}$ can caused the view direction associated with the respective initial orientations for these two locations to move from one side of the posterior direction to the other. This can cause rapid 180° flip-flopping in the perceived direction of gravity from the point of view of the virtual camera. Accordingly, if $Rot^V$ were chosen so as to simply rotate the camera about its view vector by an amount −γ when the view direction was close to the anterior-posterior direction, a sequence of images for the virtual endoscopy might appear to barrel roll erratically in 180° jumps about the centre of the rendered images (i.e. the view direction).

Accordingly, the inventors have realised that the virtual camera should not simply be rotated about its view vector by an amount −γ so as to align its down vector D with the projection vector $P_{DT}$ regardless of the magnitude of δ determined in step S11. The inventors have appreciated that in some circumstances improved results can be achieved if $Rot^V$ is calculated as a fractional amount of γ, where the fractional amount depends on δ. That is to say where $Rot^V$=−γ*fn(δ), where fn(δ) is a function that varies between zero and unity according to δ.

Figure 11:
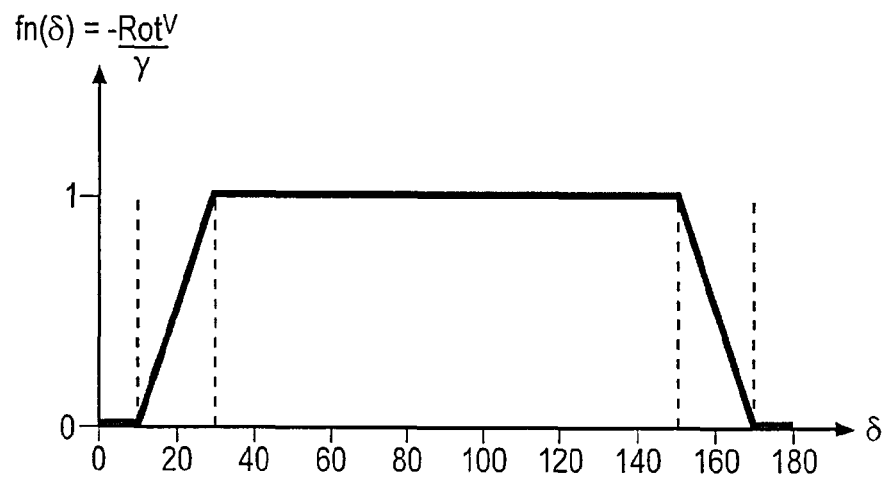
FIG. 11 is a graph schematically showing the ratio of a rotation in roll angle applied to a virtual camera to roll angle as a function of angle between a view direction for the virtual camera and a posterior direction of a data set according to an embodiment of the invention.

FIG. 11 is a graph schematically showing a form for fn(δ) which may be used at step S13 to calculate $Rot^V$. The inventors have found this form of fn(δ) provides a good balance between providing a user with a perception of virtual gravity through rotation of the virtual camera about its view vector, while avoiding barrel rolls.

For values of δ corresponding to a separation angle between the view direction and the posterior direction which is less than a predetermined no-rotation threshold, in this case 10°, fn(δ) is set to zero (that is to say $Rot^V$=−0 for values of δ between 0° and 10° and between 170° and 180°). This is because the inventors have found that it can be counter productive to attempt any reorientation of the camera for values of δ on this order because of the potential for alarming barrel roll about the view direction. For values of δ corresponding to a separation angle between the view direction and the posterior direction which is greater than a predetermined full-rotation threshold, in this case 30°, fn(δ) is set to unity (that is to say $Rot^T$=−γ for values of δ between 30° and 150°). This is because for this range of separation angle, the camera down vector D may be rotated to fully align with the projection vector $P_{DT}$ with minimal risk of barrel roll. Between the full-rotation and the no-rotation thresholds (i.e. in the ranges 10°<δ<30° and 150°<δ<180°), fn(δ) increases, in this case linearly, from unity to zero with separation angle between the view direction and the posterior direction (i.e. increasing from δ=10° to δ=30°, and decreasing from δ=150° to δ=180°. Other variations, e.g. an exponential variation, could also be used in these ranges.

The inventors have found that by varying the value of fn(δ) (and hence $Rot^V$) in the kind of way shown in FIG. 11 (i.e. in a way that depends on the initial orientation of the camera), a natural looking flythrough can be obtained which balances the advantages of providing a perception of gravity while reducing the potential for barrel roll.

For ease of explanation, values of δ considered here run from 0° to 180°. However it will be appreciated that in the general case it is the angular separation between the view vector and either of the posterior of anterior directions (i.e. with or opposite to the predetermined selected direction for the artificial gravity) which is significant. This means in general δ may be considered as being from 0° to 90° from virtual gravity down (in this example posterior), or being from 0° to 90° from virtual gravity up (here anterior). This is represent in FIG. 11 by the symmetry of the curve about δ=90°.

In step S14, the virtual camera is reoriented from its initial orientation determined for the present location based on the geometry of the lumen by a rotation of $Rot^V$ about the right axis (i.e. a pitch) as determined at step S10, and by a rotation of $Rot^V$ about the view axis (i.e. a roll) as determined at step S13. This may be achieved mathematically by determining rotation matrices for each rotation transform and applying them separately to the virtual camera, or by applying the previously determined product of the rotation matrices for each rotation transform to the virtual camera in one reorientation step.

Processing then returns to step S3. In step S3, an image for location $L_n$ is rendered from the data set according for the camera orientation obtained after applying the rotations $Rot^T$ about the right axis $Rot^V$ about the view axis in step S14. Again, the image may be rendered in any conventional manner using rendering parameters selected according to the desired appearance of the lumen of interest in the virtual endoscopy flythrough to be displayed. Typically the same rendering parameters will used for each rendered image.

Processing the proceeds to step S4 and the process of orienting the camera for rendering the next image in the virtual colonoscopy is begun. The method continues to loop through steps S3 to S14 until an image for the last location on the flight path has been rendered, at which point the virtual colonoscopy flythrough is complete. (The images, or at least the locations and orientations from where they are rendered, may be stored so a user can navigate forwards and backwards along the flight path as is conventional).

Thus during the flythrough the camera is orientated so as to tend towards a predetermined direction in the data set, in this case the posterior direction. This is achieved by pitch and roll rotations by fractional amounts of the offset between the camera down directions and respective bias directions for each of roll and pitch. By varying the fractional amount according to the initial orientation of the camera, the advantages of providing a perceived preferred direction for the rendered images is balanced with the need to maintain a good view of the lumen ahead, and to avoid barrel rolling.

It will be appreciated that the method shown in FIG. 4 may be modified in other embodiments.

For example, as noted above, and although not shown in FIG. 4 for simplicity, a rotation about the camera's right (pitch) axis which is similar to that determined in steps S9 and S10 will in general also be applied to the camera orientation defined in step S2 for the first image before the image is rendered at step S3. There is no need to calculate and execute a rotation about the camera's view (roll) axis similar that done in steps S11 and S12 for the first image because the most appropriate camera orientation about the view vector has already been selected in step S2 (i.e. the orientation that most closely aligns the down vector with the posterior direction in the data set).

Furthermore, not all of the steps will be performed in all embodiments. For example, in some embodiments the method may not include a step corresponding to step S3. Thus a series of camera orientations may be determined for a corresponding series of rendering locations, but without rendering any images. Thus the determined camera orientations may be stored for later retrieval when the flythrough is obtained. However, in general the computational overhead of calculating the orientations "on the fly" will be sufficiently small that this will be done in preference to storing and maintaining virtual camera orientation for each flythrough.

Some embodiments may not include steps corresponding to steps S11, S12 or S13 so that the camera may only be reoriented from its initial orientation about the right axis. Alternatively, some embodiments may not include steps corresponding to steps S9 or S10 so that the camera may only be reoriented from its initial orientation about the view axis.

Furthermore the steps need not be performed in the order shown in FIG. 4. For example steps S9 and S10 could be performed after steps S11, S12 and S13 with no effect on the results of the processing.

The specific way in which the steps are performed could also be modified. For example, similar results could be achieved by applying the rotation $Rot^T$ about the right axis before $Rot^V$ is determined. This will not effect the results because the two rotations and their calculation are in effect independent of one another because they are orthogonal.

Furthermore, while the above description has primarily referred to data from a CT scanner, it will be appreciated that the data could equal be obtained from other imaging modalities, for example a magnetic resonance (MR) scanner, a positron-emission tomography (PET) scanner, or an ultrasound scanner.

Furthermore still, although the above description focussed on selecting the posterior direction in the data set as a direction for an artificial gravity with which the virtual camera tends to align, any other direction in the data set could be used. In cases where a clinician would like to compare flythroughs of different data sets of the same lumen, it will be appropriate to define the same direction with respect to the patient orientation (as opposed to with respect to real world gravity) for all data sets. Thus if, as above, the posterior direction is taken to be the direction of virtual gravity, for a scan on a supine patient, the virtual gravity (posterior) direction aligns with real world gravity, but for a scan on a prone patient, the virtual gravity (still posterior) direction aligns opposite to real world gravity. Thus flythroughs of both data sets would be displayed with the same up direction at corresponding locations on the flight path. For a patient lying at an arbitrary angle during the scan, the virtual gravity will be at a corresponding arbitrary angle with respect to real world gravity.

Figure 12:
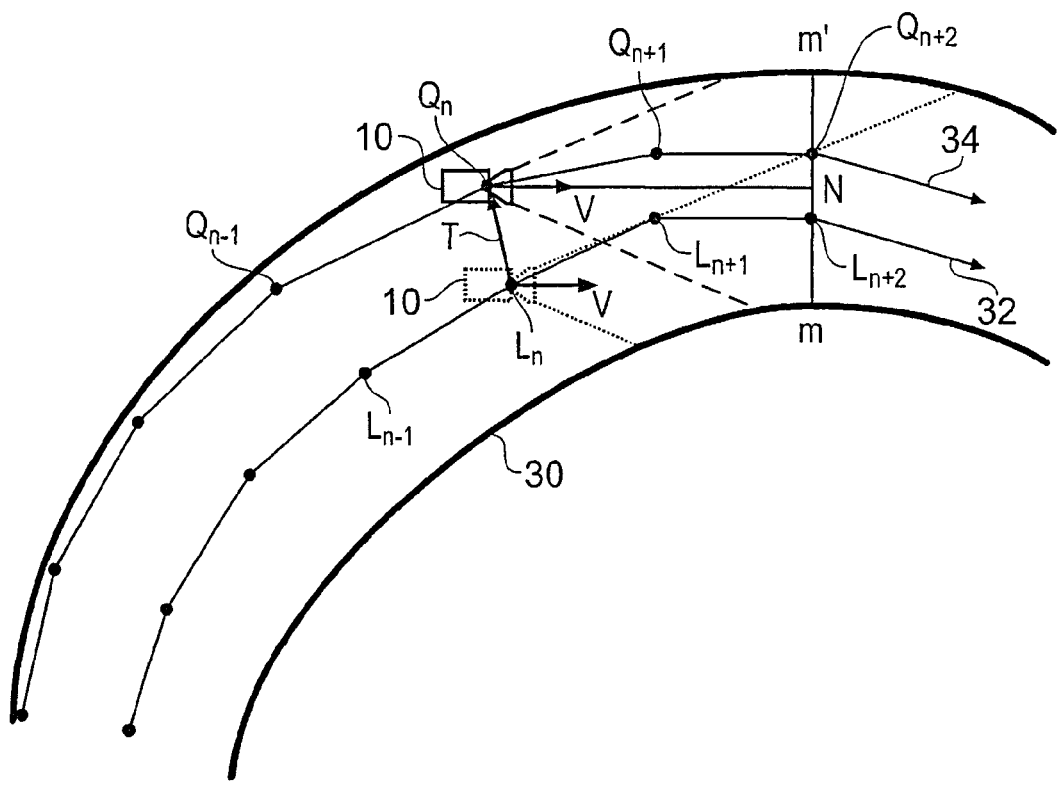
FIG. 12 schematically shows a conventional flight path for a virtual camera and a modified flight path according to an embodiment of the invention.

FIG. 12 is a schematic section view of a colon 30 taken in an arbitrary plane and showing the virtual camera 10 at two locations. A first location $L_n$ (camera 10 shown in dotted line) is on a first flight path 32 connecting between rendering locations $L_0, L_1, \ldots L_n$, such as those shown in FIGS. 2, 3, 5, 7 and 8, and calculated according to any of the known techniques. Embodiments of the invention may be applied to a flythrough along this flight path as described above. However, the second location $Q_n$ (camera 10 shown in solid line) is on a second flight path 34 which connects between rendering location $Q_0, Q_1, \ldots Q_n, \ldots$, and which has been determined in accordance with an embodiment of the invention. The second flight path 34 differs from conventionally determined flight paths in that it has been optimized for the modified virtual camera orientations provided by embodiments of the invention.

The locations $Q_n$ on the modified flight path 34 may be determined by applying a translation T which moves the camera from the corresponding location $L_n$ on the original flight path. In this case the translation T is in a direction which is normal to a tangent to the originally determined flight path 32 at location $L_n$, and in the plane containing the virtual camera's view vector V at location $L_n$. This direction may be approximated by a direction which is normal to a line connecting between $L_{n+1}$ and $L_{n+1}$, and which passes through $L_n$.

The magnitude of the translation may be defined so that it results in the virtual camera moving to a location (i.e. $Q_n$) from which the view vector V points as closely as possible to a desired location N in the lumen. For example, here the desired location N is defined to be a point midway along a line MM'. MM' is defined by the extent of the intersection of the plane containing the translation direction T and the view vector V (i.e. the plane of FIG. 12) at location $L_n$ with a plane that is normal to the view vector V and passing through location $L_{n+2}$, which is contained within the lumen.

In this example, it is possible for the camera to move to a location (i.e. $Q_n$) at which its view vector V is directed towards the desired point N corresponding to location $L_n$. However, in some cases this may not be possible without the camera moving outside of the lumen. In this case the magnitude of the translation vector T may be defined so that the camera moves as far as possible along the direction of translation T while remaining within the lumen. That is to say, the camera may be translated to a location $Q_n$ that is at the point where the translation direction intersects the lumen wall.

In other examples, different schemes may be used. For example, location $Q_n$ may be determined by moving the camera along the direction T (determined as above) by an amount that causes its view vector to point as closely as possible to a location used for determining the initial orientation of the camera at the original location $L_n$, e.g. location $L_{n+4}$ in the above example, without going outside of the lumen.

Figure 13:
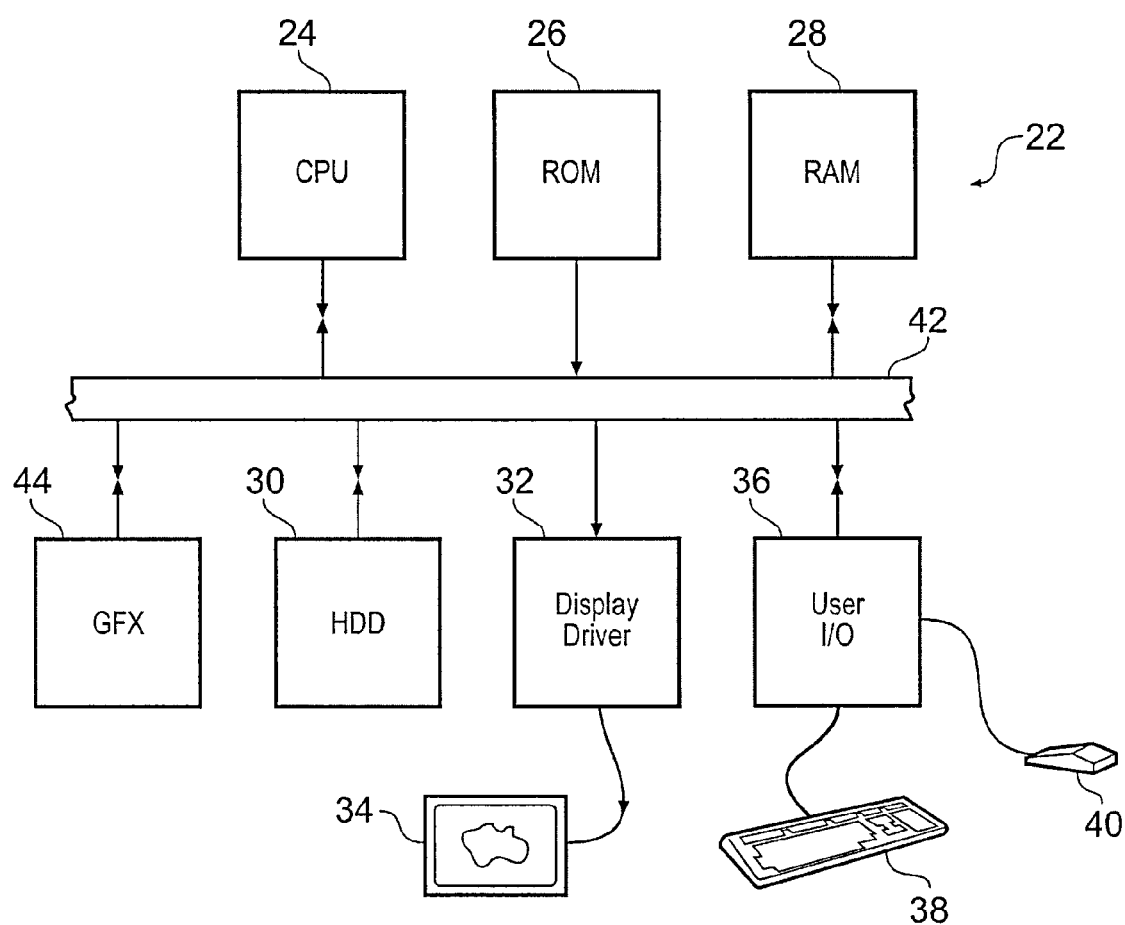
FIG. 13 schematically shows a general purpose computer system configured to process volume data sets in accordance with embodiments of the invention.

FIG. 13 schematically illustrates a general purpose computer system 22 configured to perform processing of volume data in accordance with an embodiment of the invention. The computer 22 includes a central processing unit (CPU) 24, a read only memory (ROM) 26, a random access memory (RAM) 28, a hard disk drive 30, a display driver 32 and display 34 and a user input/output (IO) circuit 36 with a keyboard 38 and mouse 40. These devices are connected via a common bus 42. The computer 22 also includes a graphics card 44 connected via the common bus 42. In this example, the graphics card is a Radeon X800XT visual processing unit manufactured by ATI Technologies Inc., Ontario Canada. The graphics card includes a graphics processing unit (GPU) and random access memory tightly coupled to the GPU (GPU memory) (not shown in FIG. 13).

The CPU 24 may execute program instructions stored within the ROM 26, the RAM 28, or the hard disk drive 30 to carry out processing of signal values associated with voxels of volume data that may be stored within the RAM 28 or the hard disk drive 30. The RAM 28 and hard disk drive 30 are collectively referred to as the system memory. The GPU may also execute program instructions to carry out processing of volume data passed to it from the CPU.

Thus a method for orienting a virtual camera for rendering a virtual endoscopy image of a lumen in a biological structure represented by a medical image data set, e.g., a colon, has been described. The method comprises selecting a location from which to render an image, determining an initial orientation for the virtual camera relative to the data set for the selected location based on the geometry of the lumen, determining an offset angle between the initial orientation and a bias direction; and orienting the virtual camera in accordance with a rotation from the initial orientation towards the bias direction by a fractional amount of the offset angle which varies according to the initial orientation. The fractional amount may vary according to the offset angle and/or a separation between a predetermined direction in the data set and a view direction of the virtual camera for the initial orientation. Thus the camera orientation can be configured to tend towards a preferred direction in the data set, while maintaining a good view of the lumen and avoiding barrel rolling effects.

For use in a hospital environment, a computer system that implements the invention may usefully be integrated with a Picture Archiving and Communication System (PACS). This is a hospital-based computerised system which can store diagnostic images of different types (including three-dimensional volume data sets from CT, MR, PET and ultrasound scanners) in a digital format organised in a single central archive. Each image has associated patient information such as the name and date of birth of the patient also stored in the archive. The archive is connected to a computer network provided with a number of workstations, so that users all around the hospital site can access and view any image data as needed. Additionally, users remote from the site may be permitted to access the archive over the internet or a wide area network.

In the context of the present invention, therefore, a plurality of volume data sets can be stored in a PACS archive, and a computer-implemented method of orienting a virtual camera for virtual endoscopy according to of embodiments of the invention can be provided on a workstation connected to the archive via a computer network. The method may be performed on a local processor comprised within the workstation, or on a central processor located elsewhere in the network.

Figure 14:
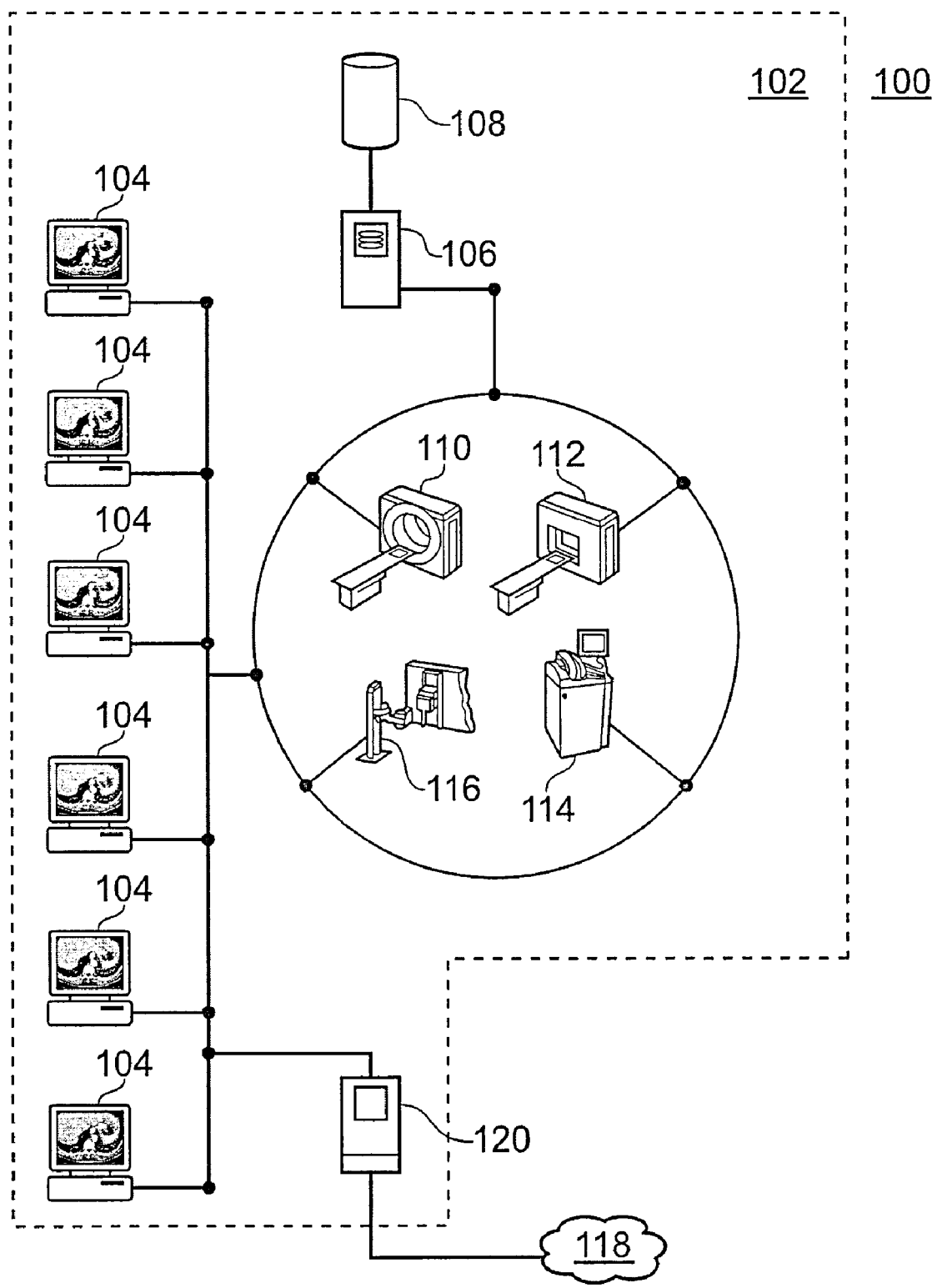
FIG. 14 shows an example computer network that can be used in conjunction with embodiments of the invention.

FIG. 14 shows an example computer network which can be used in conjunction with embodiments of the invention. The network 100 comprises a local area network in a hospital 102. The hospital 102 is equipped with a number of workstations 104 which each have access, via the local area network, to a hospital computer server 106 having an associated storage device (memory) 108. A PACS archive is stored on the storage device 108 so that data in the archive can be accessed from any of the workstations 104. One or more of the workstations 104 has access to software for computer-implementation of methods of calculating a starting point for virtual endoscopy as described above. The software may be stored locally at the or each workstation 104, or may be stored remotely and downloaded over the network 100 to a workstation 104 when needed. In another example, methods embodying the invention may be executed on the computer server 106 with the workstations 104 operating as terminals. A number of medical imaging devices 110, 112, 114, 116 are connected to the hospital computer server 106. Volume data collected with the devices 110, 112, 114, 116 can be stored directly into the PACS archive on the storage device 106. Thus camera orientations for virtual endoscopy can be calculated immediately after the corresponding volume data set is recorded, so that swift further processing/display of images corresponding to the virtual endoscopy can be made to allow rapid diagnosis in the event of a medical emergency. The local area network 100 is connected to the Internet 118 by a hospital internet server 120, which allows remote access to the PACS archive. This is of use for remote accessing of the data and for transferring data between hospitals, for example, if a patient is moved or to allow external research to be undertaken.

It will be appreciated that although particular embodiments of the invention have been described, many modifications/additions and/or substitutions may be made within the scope of the present invention. Accordingly, the particular examples described are intended to be illustrative only, and not limitative.

REFERENCES

[1] U.S. Pat. No. 5,971,767
[2] U.S. Pat. No. 6,496,188
[3] U.S. Pat. No. 6,343,936
[4] U.S. Pat. No. 5,611,025
[5] US 2005/0033114
[6] US 2004/0202990
[7] WO 03/054803
[8] U.S. Pat. No. 5,782,762
[9] U.S. Pat. No. 6,083,162
[10] D. Bartz, "Virtual endoscopy in research and clinical practice", STAR—State of the Art Report, Eurographics 2003, The DEurographics Association
[11] Huang, A., Roy, D., Franaszek, M., Summers, R. M., Teniae Coli Guided Navigation and Registration for Virtual Colonoscopy IEEE, Visualization 2005:36

[12] Wyatt, C. L., Ge, Y., Vining, D, J., Automatic Segmentation of the Colon for Virtual Colonoscopy, Computerized Medical Imaging and Graphics, 24, 1, 1-9, 2000.

[13] Frimmel, H., Nappi. J., Yoshida, H., Centerline-based Colon Segmentation for CT Colonography, Medical Physics, 32, 8, 2665-2672, August 2005

What is claimed is:

1. A method of orienting a virtual camera for rendering a virtual endoscopy image of a lumen in a biological structure represented by a medical image data set, the method comprising:
   (a) selecting a location from which to render an image;
   (b) determining an initial orientation for the virtual camera relative to the data set for the: selected location based on the geometry of the lumen;
   (c) determining an offset angle between the initial orientation and a bias direction, wherein the bias direction corresponds to a predetermined direction in the data set; and
   (d) orienting the virtual camera in accordance with a rotation from the initial orientation towards the bias direction by a fractional amount of the offset angle which varies according to the initial orientation.

2. The method of claim 1, wherein the fractional amount varies according to the offset angle.

3. The method of claim 2, wherein the fractional amount is unity if the offset angle is less than a predetermined full-rotation threshold.

4. The method of claim 3, wherein the predetermined full-rotation threshold is selected from the group consisting of 1°, 2°, 3°, 4°, 5°, 6°, 7°, 8°, 9°, 10°, 11°, 12°, 13°, 14° and 15°.

5. The method of claim 2, wherein the fractional amount is zero if the offset angle is greater than a predetermined no-rotation threshold.

6. The method of claim 5, wherein the predetermined no-rotation threshold is selected from the group consisting of 15°, 20°, 25°, 30°, 35°, 40°, 45° and 50°.

7. The method of claim 2, wherein the fractional amount varies between zero and unity if the offset angle is within a predetermined partial-rotation range.

8. The method of claim 7, wherein the predetermined partial-rotation range has a lower boundary selected from the group consisting of 0°, 1°, 2°, 3°, 4°, 5°, 6°, 7°, 8°, 9°, 10°, 11°, 12°, 13°, 14° and 15° and an upper boundary selected from the group consisting of 15°, 20°, 25°, 30°, 35°, 40°, 45° and 50°.

9. The method of claim 7, wherein the fractional amount decreases linearly with increasing offset angle within the predetermined partial-rotation range.

10. The method of claim 7, wherein the fractional amount decreases exponentially with increasing offset angle within the predetermined partial-rotation range.

11. The method of claim 1, wherein the fractional amount varies according to an angular separation between a predetermined direction in the data set and a view direction of the virtual camera for the initial orientation.

12. The method of claim 11, wherein the predetermined direction is aligned with a posterior direction of the biological structure.

13. The method of claim 11, wherein the data set comprises voxels arranged along three orthogonal data set axes, and the predetermined direction is aligned with one of the data set axes.

14. The method of claim 11, wherein the fractional amount is zero if the angular separation is less than a predetermined no-rotation threshold.

15. The method of claim 14, wherein the predetermined no-rotation threshold is selected from the group consisting of 1°, 2°, 3°, 4°, 5°, 6°, 7°, 8°, 9°, 10°, 11°, 12°, 13°, 14°, 15°, 16°, 17°, 18°, 19° and 20°.

16. The method of claim 14, wherein the predetermined full-rotation threshold is selected from the group consisting of 15°, 20°, 25°, 30°, 35°, 40°, 45° and 50°.

17. The method of claim 11, wherein the fractional amount is unity if the angular separation is greater than a predetermined full-rotation threshold.

18. The method of claim 11, wherein the fractional amount varies between zero and unity if the angular separation is within a predetermined partial-rotation range.

19. The method of claim 18, wherein the predetermined partial-rotation range has a lower boundary selected from the group consisting of 0°, 1°, 2°, 3°, 4°, 5°, 6°, 7°, 8°, 9°, 10°, 11°, 12°, 13°, 14°, 15°, 16°, 17°, 18°, 19° and 20° and an upper boundary selected from the group consisting of 15°, 20°, 25°, 30°, 35°, 40°, 45° and 50°.

20. The method of claim 19, wherein the fractional amount increases linearly with increasing angular separation within the predetermined partial-rotation range.

21. The method of claim 19, wherein the fractional amount increases exponentially with increasing angular separation within the predetermined partial-rotation range.

22. The method of claim 1, wherein the virtual camera is orientable about orthogonal roll, pitch and yaw axes, the roll axis being aligned with a view direction for the virtual camera, and wherein the bias direction comprises a projection of a predetermined direction in the data set onto a plane containing the roll and yaw axes for the initial orientation.

23. The method of claim 22, wherein the predetermined direction in the data set is aligned with a posterior direction of the biological structure.

24. The method of claim 22, wherein the data set comprises voxels arranged along three orthogonal data set axes, and the predetermined direction is aligned with one of the data set axes.

25. The method of claim 1, wherein the virtual camera is orientable about orthogonal roll, pitch and yaw axes, the roll axis being aligned with a view direction for the virtual camera, and wherein the bias direction comprises a projection of a predetermined direction in the data set onto a plane containing the pitch and yaw axes for the initial orientation.

26. The method of claim 25, wherein the predetermined direction in the data set is aligned with a posterior direction for the biological structure.

27. The method of claim 25, wherein the data set comprises voxels arranged along three orthogonal data set axes, and the predetermined direction is aligned with one of the data set axes.

28. The method of claim 1, wherein step (b) includes determining a desired orientation for the virtual camera relative to the data set for the selected location based on the geometry of the lumen, determining a relocation angle between the desired orientation of the virtual camera and a previous orientation of the virtual camera, and determining the initial orientation of the virtual camera to be the desired orientation if the relocation angle is greater than a relocation angle threshold, and otherwise maintaining the previous orientation as the initial orientation.

29. The method of claim 28, wherein the relocation angle threshold is selected from the group consisting of 1°, 2°, 3°, 4°, 5°, 6°, 7°, 8°, 9° and 10°.

30. The method according to claim 1, further comprising translating the virtual camera from the selected location on the flight path to a new location, wherein the new location is determined in accordance with the geometry of the lumen and the orientation of the camera after the rotation from the initial orientation towards the bias direction by a fractional amount of the offset angle which varies according to the initial orientation.

31. The method according to claim 1, further comprising rendering an image for the selected location and orientation of the virtual camera.

32. The method of claim 31, further comprising displaying the rendered image on a display.

33. A method of virtual endoscopy comprising displaying a series of images rendered according to claim 31 from a corresponding series of selected locations along a navigation path through a lumen.

34. A method of orienting a virtual camera for rendering a virtual endoscopy image of a lumen in a biological structure represented by a medical image data set, the method comprising:
  (a) selecting a location from which to render an image;
  (b) determining an initial orientation for the virtual camera relative to the data set for the: selected location based on the geometry of the lumen;
  (c) determining an offset angle between the initial orientation and a bias direction; and
  (d) orienting the virtual camera in accordance with a rotation from the initial orientation towards the bias direction by a fractional amount of the offset angle which varies according to the initial orientation, wherein the fractional amount varies according to the offset angle.

35. A method of orienting a virtual camera for rendering a virtual endoscopy image of a lumen in a biological structure represented by a medical image data set, the method comprising:
  (a) selecting a location from which to render an image;
  (b) determining an initial orientation for the virtual camera relative to the data set for the: selected location based on the geometry of the lumen;
  (c) determining an offset angle between the initial orientation and a bias direction; and
  (d) orienting the virtual camera in accordance with a rotation from the initial orientation towards the bias direction by a fractional amount of the offset angle which varies according to the initial orientation, wherein the fractional amount varies according to an angular separation between a predetermined direction in the data set and a view direction of the virtual camera for the initial orientation.

36. A computer program product comprising machine readable instructions stored on a non-transitory computer-readable storage medium for implementing the method of claim 1.

37. A computer programmed to perform the method of claim 1.

38. A network including a data storage and a computer according to claim 37.

39. An apparatus comprising a processing unit programmed to implement the method of claim 1.

* * * * *